United States Patent
Bachovchin et al.

(10) Patent No.: US 8,513,187 B2
(45) Date of Patent: Aug. 20, 2013

(54) SOFT PROTEASE INHIBITORS, AND PRO-SOFT FORMS THEREOF

(75) Inventors: William W. Bachovchin, Cambridge, MA (US); Hung-sen Lai, Andover, MA (US); Wengen Wu, Medford, MA (US)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 13/203,651

(22) PCT Filed: Mar. 1, 2010

(86) PCT No.: PCT/US2010/025771
§ 371 (c)(1),
(2), (4) Date: Mar. 28, 2012

(87) PCT Pub. No.: WO2010/099537
PCT Pub. Date: Sep. 2, 2010

(65) Prior Publication Data
US 2012/0178677 A1    Jul. 12, 2012

Related U.S. Application Data

(60) Provisional application No. 61/156,246, filed on Feb. 27, 2009.

(51) Int. Cl.
*A61K 38/28* (2006.01)
*A61P 5/50* (2006.01)

(52) U.S. Cl.
USPC ............................................. 514/6.5; 514/1.1

(58) Field of Classification Search
None
See application file for complete search history.

(56) References Cited

FOREIGN PATENT DOCUMENTS

| WO | WO 2005/082348 | 9/2005 |
|---|---|---|
| WO | WO 2005/119526 | 10/2005 |
| WO | WO-2007/100374 A2 | 9/2007 |
| WO | WO 2007100374 A2 * | 9/2007 |
| WO | WO-2008/118848 A1 | 10/2008 |

OTHER PUBLICATIONS

Supplementary European Search Report for EP 10 74 6977 dated Jun. 27, 2012.
International Search Report for PCT/US2010/025771 dated May 10, 2010.

* cited by examiner

*Primary Examiner* — Cecilia J Tsang
*Assistant Examiner* — Randall L Beane
(74) *Attorney, Agent, or Firm* — Dana M. Gordon; Foley Hoag LLP

(57) ABSTRACT

The invention provides compounds and methods for inhibiting proteases. One aspect of the invention features pro-soft inhibitors which react with an activating protease to release an active inhibitor moiety in proximity to a target protease. In certain instances, compounds inhibit proteasomes and/or post-proline cleaving enzymes (PPCE), such as dipeptidyl peptidase IV. The compounds of the invention provide a better therapeutic index, owing in part to reduced toxicity and/or improved specificity for the targeted protease. Another aspect of the invention provides for the use of the disclosed compounds for treating Type II diabetes, insulin resistance, glucose intolerance, hyperglycemia, hypoglycemia, hyperinsulinemia, obesity, hyperlipidemia, or hyperlipoproteinemia.

2 Claims, 18 Drawing Sheets

Figure 6

| Compound | Structure | CLogP* | In Vitro IC$_{50}$** | | | | | Intracellular IC$_{50}$** |
|---|---|---|---|---|---|---|---|---|
| | | | DPP IV | DPP8 | DPP9 | FAP | PREP | |
| 6 | 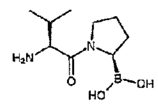 | -1.22 | 0.4 nM | 2.9 nM | 1.8 nM | 14 nM | 56.7 nM | 80 nM |
| 7 | 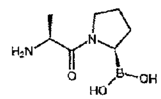 | -2.15 | 0.2 nM | 5.8 nM | 3.4 nM | 65.7 nM | 214 nM | 10.3 µM |
| 8 | 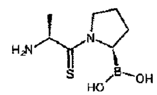 | -1.42 | 0.1 nM | 0.6 nM | 1.1 nM | 51.8 nM | 116 nM | 199 nM |
| 9 | 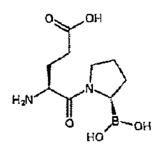 | -3.28 | 1.2 nM | 28.4 nM | 19.8 nM | 5.3 nM | 668 nM | 33 µM |
| 10 | 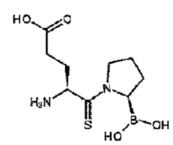 | -4.74 | 0.9 nM | 1.3 nM | 14.3 nM | 4 nM | 1.2 µM | 5.4 µM |
| 11 | 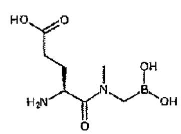 | -5.56 | 26.4 nM | 55.9 µM | 11.4 µM | 9.1 µM | >10 µM | >1 mM |

Figure 7

| Compound | Structure | CLogP* | In Vitro IC₅₀** | | | | | Intracellular IC₅₀** |
|---|---|---|---|---|---|---|---|---|
| | | | DPP IV | DPP8 | DPP9 | FAP | PREP | |
| 5 | 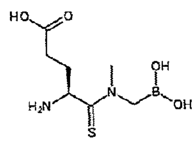 | -5.36 | 0.4 nM | 5.3 μM | 2.4 μM | 1.3 μM | >100 μM | 828 μM |
| 12 | 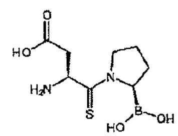 | -2.33 | 2.1 nM | 50.4 nM | 62.3 nM | 234 nM | 1.9 μM | 14.2 μM |
| 13 | 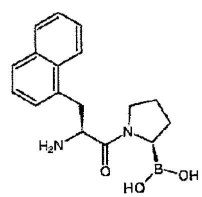 | 0.44 | 1.6 nM | 15 nM | 10.2 nM | 153 nM | | 89.2 nM |
| 14 | 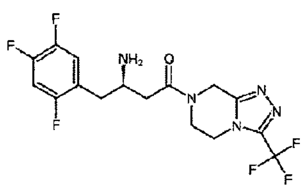 | 0.69 | 1.1 nM | 25.4 μM | 35.6 μM | 87.8 μM | >100 μM | 213 μM |

Figure 8

| Compound | Structure | CLogP* | In Vitro IC$_{50}$** | | | | | Intracellular IC$_{50}$** |
|---|---|---|---|---|---|---|---|---|
| | | | DPP IV | DPP8 | DPP9 | FAP | PREP | |
| 15 | 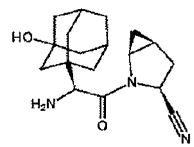 | -0.02 | 1 nM | 197 nM | 54 nM | 2.6 μM | >100 μM | 512 nM |
| 16 | 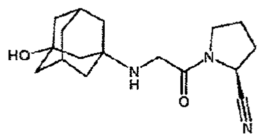 | 0.69 | 1.9 nM | 1.4 μM | 62.5 nM | 7.6 μM | 37.1 μM | 1 μM |
| 17 | 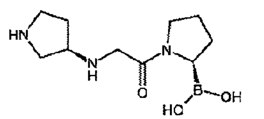 | -1.01 | 11 nM | 2.3 μM | 294 nM | 1.8 μM | | 123 μM |
| 18 | 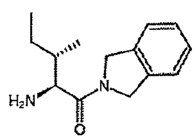 | 1.63 | 2.8 μM | 252 nM | 149 nM | 15.6 μM | >100 μM | 1 μM |
| 19 | 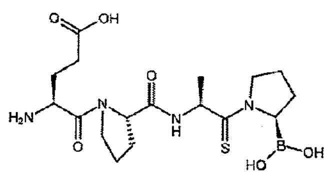 | -4.44 | 11.3 nM | 14.3 μM | 13.5 μM | 43.2 μM | | 20.1 μM |

Figure 9

| Compound | Structure | CLogP* | In Vitro IC₅₀** | | | | | Intracellular IC₅₀** |
|---|---|---|---|---|---|---|---|---|
| | | | DPP IV | DPP8 | DPP9 | FAP | PREP | |
| 20 | 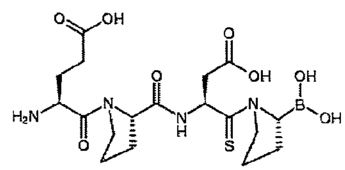 | -5.00 | 540 nM | >10 μM | 86 μM | >100 μM | | 183 μM |
| 21 | 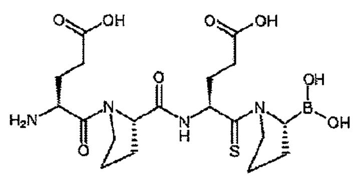 | -5.14 | 400 nM | >10 μM | 96.6 μM | 14.3 μM | | 298 μM |

22

A.

23

B.

C.

IC50 pH 2 = 3.82 nM (nanomolar)

IC50 pH 8 = 31 uM (micromolar)

A.

24

B.

C.

IC50 pH 2 = 4.5 uM (micromolar)

A.

25

B.

C.

IC50 pH 2 = 46 nM (nanomolar)
IC50 pH 8 = 496 uM (micromolar)

A.

26

B.

C.

IC50 pH 2 = 18 nM (nanomolar)
IC50 pH 8 = 166 uM (micromolar)

A.

27

B.

IC50 pH 2= 0.48 uM (micromolar)
IC50 pH 8= 1 mM (millimolar)

A.

28

B.

A.

29

B.

C.

|  | DPP4 | DPP8 | DPP9 |
|---|---|---|---|
| Sigmoidal dose-response (variable slope) | | | |
| Best-fit values | | | |
| Bottom | = 0.0 | = 0.0 | = 0.0 |
| Top | 102.7 | 100.4 | 100.6 |
| LogEC50 | -8.323 | -6.699 | -6.815 |
| HillSlope | -1.260 | -0.7924 | -1.022 |
| EC50 | 4.751e-009 | 2.000e-007 | 1.530e-007 |

DPP4 = 4.75nM
DPP8 = 200nM
DPP9 = 153nM

30

SOFT PROTEASE INHIBITORS, AND PRO-SOFT FORMS THEREOF

RELATED APPLICATIONS

This application is a 371 national stage application based on Patent Cooperation Treaty Application serial number PCT/US2010/025771, filed Mar. 1, 2010; which claims the benefit of priority to U.S. Provisional Patent Application Ser. No. 61/156,246, filed Feb. 27, 2009.

BACKGROUND OF THE INVENTION

Proteases are enzymes that cleave proteins at specific peptide bonds. Proteases can be classified into four generic classes: serine, thiol or cysteinyl, acid or aspartyl, and metalloproteases (Cuypers et al., *J. Biol. Chem.* 1982, 257, 7086. Proteases are essential to a variety of biological activities, such as digestion, formation and dissolution of blood clots, reproduction, and immune reaction to foreign cells and organisms. However, aberrant proteolysis is associated with a number of diseases in humans and other mammals. Accordingly, it is often beneficial to disrupt the function of one or more proteolytic enzymes in the course of treating a patient.

The binding site for a peptide substrate consists of a series of "specificity subsites" across the surface of the enzyme. The term "specificity subsite" refers to a pocket or other site on the enzyme capable of interacting with a portion of a substrate for the enzyme. In discussing the interactions of peptides with proteases, e.g., serine and cysteine proteinases, the present application utilizes the nomenclature of Schechter and Berger (*Biochem. Biophys. Res. Commun.* 1967, 27, 157-162). The individual amino acid residues of a substrate or inhibitor are designated P1, P2, etc. and the corresponding subsites of the enzyme are designated S1, S2, etc., starting with the carboxy terminal residue produced in the cleavage reaction. The scissile bond of the substrate is the amide bond between P1-P1' of the substrate. Thus, for a peptide Xaa1-Xaa2-Xaa3-Xaa4, which is cleaved between the Xaa3 and Xaa4 residues, the Xaa3 residue is referred to as the P1 residue and binds to the S1 subsite of the enzyme, Xaa2 is referred to as the P2 residue and binds to the S2 subsite, and so forth.

Dipeptidyl peptidase IV (DPIV or DPPIV) is a serine protease that cleaves N-terminal dipeptides from a peptide chain containing, preferably, a proline residue in the penultimate position, e.g., in the P1 position. DPIV belongs to a group of cell-membrane-associated peptidases and, like the majority of cell-surface peptidases, is a type II integral membrane protein, being anchored to the plasma membrane by its signal sequence. DPIV is found in a variety of differentiated mammalian epithelia, endothelia and hematopoetic cells and tissues, including those of lymphoid origin where it is found specifically on the surface of CD4$^+$ T cells. DPIV has been identified as the leukocyte differentiation marker CD26.

Proteasomes are cellular complexes comprising proteases responsible for the majority of intracellular protein turnover in eukaryotic cells, including proteolytic degradation of damaged, oxidized or misfolded proteins, as well as processing or degradation of key regulatory proteins required for various cellular functions, such as cell cycle progression. For example, the 26S proteasome is a multi-catalytic protease comprising at its catalytic core the 20S proteasome, a multi-subunit complex of approximately 700 kDa molecular weight. While serving an essential physiological role, the proteasome is also responsible for the inappropriate or accelerated protein degradation that occurs as a result or cause of pathological conditions in which normal cellular processes become disregulated. One notable example is cancer, in which the unregulated proteasome-mediated degradation of cell cycle regulatory proteins, including cyclins, cyclin dependent kinase inhibitors, and tumor suppressor genes, results in accelerated and uncontrolled mitosis, thereby promoting cancer growth and spread. (Goldberg et al. *Chem. & Biol.* 1995, 2, 503-508; Coux et al. *Ann. Rev. Biochem.*, 1996, 65, 801-847; Deshaies, *Trends Cell Biol.* 1995, 5, 428-434). Inhibition of proteasome enzymatic function holds promise in arresting or blunting disease progression in disease states such as cancer or inflammation.

Proteasome inhibitors, e.g., lactacystin and its analogs, have been shown to block the development of the preerythrocytic and erythrocytic stages of Plasmodium spp, the malaria parasites. During both its hepatic and erythrocytic stages, the parasite undergoes radical morphological changes and many rounds of replication, events that likely require proteasome activity. Lactacystin has been found to covalently modify the catalytic N-terminal threonines of the active sites of proteasomes, inhibiting the activity of all proteasomes examined, including those in mammalian cells, protozoa, and archeae. (Gantt et al. *Antimicrob. Agents Chemother.* 1998, 42, 2731-2738).

The human fibroblast activation protein (FAPα) is a $M_r$ 95,000 cell surface molecule originally identified with monoclonal antibody (mAb) F19 (Rettig et al. *Proc. Natl. Acad. Sci. USA* 1988, 85, 3110-3114; Rettig et al. *Cancer Res.* 1993, 53, 3327-3335). The FAPα cDNA codes for a type II integral membrane protein with a large extracellular domain, transmembrane segment, and short cytoplasmic tail (Scanlan et al. *Proc. Natl. Acad. Sci. USA* 1994, 91, 5657-5661; WO 97/34927). FAPα shows 48% amino acid sequence identity to the T-cell activation antigen CD26, also known as dipeptidyl peptidase IV (DPP IV), a membrane-bound protein with dipeptidyl peptidase activity (Scanlan et al.). FAPα has enzymatic activity and is a member of the serine protease family, with serine 624 being critical for enzymatic function (WO 97/34927). Work using a membrane overlay assay revealed that FAPα dimers are able to cleave Ala-Pro-7-amino-4-trifluoromethyl coumarin, Gly-Pro-7-amino-4-trifluoromethyl coumarin, and Lys-Pro-7-amino-4-trifluoromethyl coumarin dipeptides (WO 97/34927).

FAPα is selectively expressed in reactive stromal fibroblasts of many histological types of human epithelial cancers, granulation tissue of healing wounds, and malignant cells of certain bone and soft tissue sarcomas. Normal adult tissues are generally devoid of detectable FAPα, but some foetal mesenchymal tissues transiently express the molecule. In contrast, most of the common types of epithelial cancers, including >90% of breast, non-small-cell lung, and colorectal carcinomas, contain FAPα-reactive stromal fibroblasts (Scanlan et al.). These FAPα$^+$ fibroblasts accompany newly-formed tumor blood vessels, forming a distinct cellular compartment interposed between the tumor capillary endothelium and the basal aspect of malignant epithelial cell clusters (Welt et al. *J. Clin. Oncol.* 1994, 12, 1193-1203). While FAPα$^+$ stromal fibroblasts are found in both primary and metastatic carcinomas, the benign and premalignant epithelial lesions tested (Welt et al.), such as fibroadenomas of the breast and colorectal adenomas, only rarely contain FAPα$^+$ stromal cells. Based on the restricted distribution pattern of FAPα in normal tissues and its uniform expression in the supporting stroma of many malignant tumors, clinical trials with $^{131}$I-labeled mAb F19 have been initiated in patients with metastatic colon carcinomas (Welt et al.).

SUMMARY OF THE INVENTION

The invention provides compounds and methods for inhibiting proteases. One aspect of the invention features pro-soft inhibitors which react with an activating protease to release an active inhibitor moiety in proximity to a target protease. In certain instances, compounds inhibit proteasomes and/or post-proline cleaving enzymes (PPCE), such as dipeptidyl peptidase IV. The compounds of the invention provide a better therapeutic index, owing in part to reduced toxicity and/or improved specificity for the targeted protease.

BRIEF DESCRIPTION OF THE DRAWINGS

FIG. 6 depicts a table outlining various in vitro and in vivo assay results for DPP inhibitors. CLogP values were calculated using ChemDraw Ultra version 11.0. All of the $IC_{50}$ measurements in the table were taken from samples involving preincubating freshly prepared pH 2.0 stocks at room temperature for 4 h. All except PREP used the same substrate (GP-AMC), but different concentrations (10 μM for DPP IV, 25 μM for DPP8 and DPP9, and 50 μM for FAP).

FIG. 7 depicts a table outlining various in vitro and in vivo assay results for DPP inhibitors. CLogP values were calculated using ChemDraw Ultra version 11.0. All of the $IC_{50}$ measurements in the table were taken from samples involving preincubating freshly prepared pH 2.0 stocks at room temperature for 4 h. All except PREP used the same substrate (GP-AMC), but different concentrations (10 μM for DPP IV, 25 μM for DPP8 and DPP9, and 50 μM for FAP).

FIG. 8 depicts a table outlining various in vitro and in vivo assay results for DPP inhibitors. CLogP values were calculated using ChemDraw Ultra version 11.0. All of the $IC_{50}$ measurements in the table were taken from samples involving preincubating freshly prepared pH 2.0 stocks at room temperature for 4 h. All except PREP used the same substrate (GP-AMC), but different concentrations (10 μM for DPP IV, 25 μM for DPP8 and DPP9, and 50 μM for FAP).

FIG. 9 depicts a table outlining various in vitro and in vivo assay results for DPP inhibitors. CLogP values were calculated using ChemDraw Ultra version 11.0. All of the $IC_{50}$ measurements in the table were taken from samples involving preincubating freshly prepared pH 2.0 stocks at room temperature for 4 h. All except PREP used the same substrate (GP-AMC), but different concentrations (10 μM for DPP IV, 25 μM for DPP8 and DPP9, and 50 μM for FAP).

DETAILED DESCRIPTION OF THE INVENTION

Overview

Figure 1:
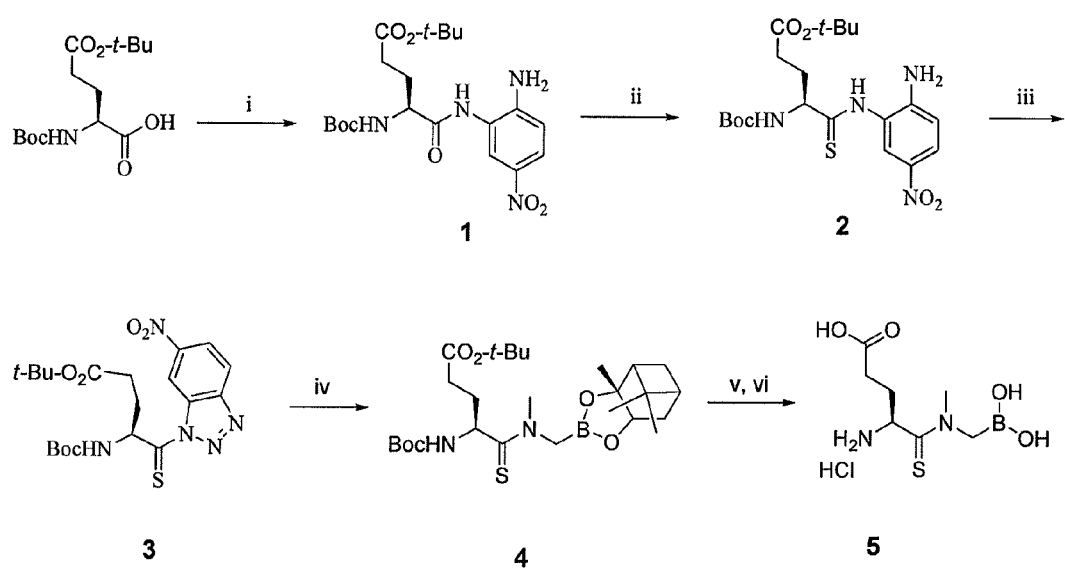
FIG. 1 depicts an exemplary reaction scheme for the formation of compound 5. Reagents and conditions: i. (a) NMM, isobutyl chloroformate, −20° C., (b) 4-nitro-1,2-phenyleneamine, −15° C. to r.t.; ii. $P_4S_{10}$, THF, 0° C. to r.t.; iii. $NaNO_2$, 0° C.; iv. BoroSar-pn.HCl, $NEt_3$, 0° C. to r.t.; v. HCl(g), $CH_2Cl_2$, 0° C. to r.t.; vi. $PhB(OH)_2$, $MTBE-H_2O$, r.t.

The present invention provides protease inhibitors and methods of using protease inhibitors. The invention features inhibitors for a wide array of proteases. For example, the protease may be a post-proline cleaving enzyme (PPCE), such as dipeptidyl peptidase IV. The invention also provides compounds that inhibit proteasome activity. In certain instances, the protease inhibitor is a pro-soft inhibitor. A pro-soft inhibitor is an inactive agent that is activated, i.e., cleaved by an "activating protease," to release an active inhibitor moiety in proximity to a "target protease." The identity of the activating protease and target protease can be the same or different. After activation of the pro-soft inhibitor, the active inhibitor moiety undergoes self-inactivation by irreversible proto-deboronation.

One of the features that makes the pro-soft inhibitor molecules of the current invention different from typical prodrugs is that the inhibitor moiety, after being generated in the active form near the target, undergoes inactivation over time, e.g., as it diffuses away from the target enzyme, thereby reducing the possibility of deleterious side effects that may result from inhibition of enzymes occurring in other parts of the patient. This combination of being released in an active form in the vicinity of the target enzyme together with this "programmed" deactivation mechanism makes the molecules of the invention more specific, effective, and safer (i.e., having fewer side effects) than the inhibitor moiety used on its own.

Advantageous features for compounds of the present invention include: better therapeutic indices, owing in part to reduced toxicity and/or improved specificity for the targeted protease; better oral availability; increased shelf-life; and/or increased duration of action (such as single oral dosage formulations which are effective for more than about 4 hours, more than about 8, more than about 12, or more than about 16 hours).

Another advantageous feature for compounds of the present invention is that proto-deboronation irreversibly releases innocuous boric acid. The $LD_{50}$ of boric acid is approximately equal to that of common table salt. Accordingly, long-term chronic therapy with the compounds of the present invention is expected to yield an improved safety profile (fewer side effects).

The compounds of the present invention can be used as part of treatments for a variety of disorders or conditions, such as those which are mediated by DPIV. While not wishing to be bound by any particular theory, it has been observed that compounds which inhibit DPP IV are able to improve glucose tolerance through mechanisms involving DPP IV inhibition.

Certain of the subject compounds have extended duration. Accordingly, in certain embodiments, the compound is selected, and the amount of compound formulated, to provide a dosage which inhibits serum PPCE (e.g., DPIV) levels by at least about 50% for at least about 4 hours after a single dose, or for at least about 8 hours, at least about 12, or at least about 16 hours after a single dose.

For instance, in certain embodiments the method involves administration of a DPIV inhibitor, preferably at a predetermined time(s) during a 24-hour period, in an amount effective to improve one or more aberrant indices associated with glucose metabolism disorders.

DEFINITIONS

A compound is said to have an "insulinotropic activity" if it is able to stimulate, or cause the stimulation of, the synthesis or expression of the hormone insulin.

The term "boro-Xaa", where Xaa is an amino acid residue, refers to the analog of an amino acid in which the carboxylate group (COOH) is replaced with a boronyl group (B(OH)$_2$). For example, the term "boro-Ala" refers to the analog of alanine in which the carboxylate group (COOH) is replaced with a boronyl group (B(OH)$_2$); and the term "boro-Pro" refers to the analog of proline in which the carboxylate group (COOH) is replaced with a boronyl group (B(OH)$_2$). In other words, the term "Ala-boroPro" refers to

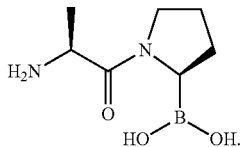

The term "thioxam" used in association with chemical nomenclature refers to a compound wherein at least one amide group has been replaced by at least one thioxamide group. For example Pro(thioxam) refers to a proline residue wherein the amide group has been replaced by a thioxamide group. For example, the term "Ala-boroPro thioxo amide" refers to

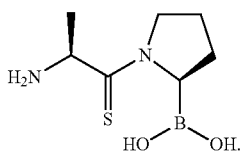

A "patient" or "subject" to be treated by the subject method can mean either a human or non-human subject. Non-human subjects include farm animals (e.g., cows, horses, pigs, sheep) and companion animals (e.g., cats, dogs).

The term "ED$_{50}$" means the dose of a drug that, in 50% of patients, will provide a clinically relevant improvement or change in a physiological measurement, such as glucose responsiveness, increase in hematocrit, decrease in tumor volume, etc.

The term "IC$_{50}$" means the dose of a drug that inhibits a biological activity by 50%, e.g., the amount of compound required to inhibit at least 50% of DPIV (or other PPCE) activity in vivo.

The term "LD$_{50}$" means the dose of a drug that is lethal in 50% of test subjects.

The term "therapeutic index" refers to the therapeutic index of a drug defined as LD$_{50}$/ED$_{50}$.

A "therapeutically effective amount" of a compound, e.g., such as a DPIV inhibitor of the present invention, with respect to the subject method of treatment, refers to an amount of the compound(s) in a preparation which, when administered as part of a desired dosage regimen (to a mammal, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

A "single oral dosage formulation" is a dosage which provides an amount of drug to produce a serum concentration at least as great as the EC$_{50}$ for that drug, but less than the LD$_{50}$. Another measure for a single oral dosage formulation is that it provides an amount of drug necessary to produce a serum concentration at least as great as the IC$_{50}$ for that drug, but less than the LD$_{50}$. By either measure, a single oral dosage formulation is preferably an amount of drug which produces a serum concentration at least 10% less than the LD$_{50}$, and even more preferably at least 50%, 75%, or even 90% less than the drug's the LD$_{50}$.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., C$_1$-C$_{30}$ for straight chains, C$_3$-C$_{30}$ for branched chains), and more preferably 20 or fewer.

"Cycloalkyl" means mono- or bicyclic or bridged saturated carbocyclic rings, each having from 3 to 12 carbon atoms. Likewise, preferred cycloalkyls have from 5-12 carbon atoms in their ring structure, and more preferably have 6-10 carbons in the ring structure.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywherein the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkenyl, and —(S)—$(CH_2)_m$—$R^1$, wherein m and $R^1$ are defined below. Representative alkylthio groups include methylthio, ethylthio, and the like.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R^1$, where m and $R_1$ are described below.

The terms "amine" and "amino" are art-recognized and refer to both unsubstituted and substituted amines, e.g., a moiety that can be represented by the formulae:

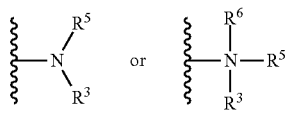

wherein $R^3$, $R^5$ and $R^6$ each independently represent a hydrogen, an alkyl, an alkenyl, —$(CH_2)_m$—$R^1$, or $R^3$ and $R^5$ taken together with the N atom to which they are attached complete a heterocycle having from 4 to 8 atoms in the ring structure; $R^1$ represents an alkenyl, aryl, cycloalkyl, a cycloalkenyl, a heterocyclyl, or a polycyclyl; and m is zero or an integer in the range of 1 to 8. In certain embodiments, only one of $R^3$ or $R^5$ can be a carbonyl, e.g., $R^3$, $R^5$, and the nitrogen together do not form an imide. In even more certain embodiments, $R^3$ and $R^5$ (and optionally $R^6$) each independently represent a hydrogen, an alkyl, an alkenyl, or —$(CH_2)_m$—$R^1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a conjugate acid with a $pK_a \geq 7.00$, i.e., the protonated forms of these functional groups have $pK_a$s relative to water above about 7.00.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 6- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like.

The terms "heterocyclyl" or "heterocyclic group" refer to 3- to 12-membered ring structures, more preferably 5- to 12-membered rings, more preferably 6- to 10-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "carbonyl" is art-recognized and includes such moieties as can be represented by the formula:

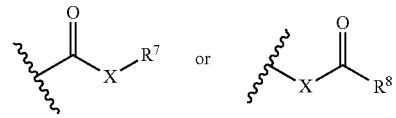

wherein X is a bond or represents an oxygen or a sulfur, and $R^7$ represents a hydrogen, an alkyl, an alkenyl, —$(CH_2)_m$—$R^1$ or a pharmaceutically acceptable salt, $R^8$ represents a hydrogen, an alkyl, an alkenyl or —$(CH_2)_m$—$R^1$, where m and $R^1$ are as defined above. Where X is an oxygen and $R^7$ or $R^8$ is not hydrogen, the formula represents an "ester." Where X is an oxygen, and $R^7$ is as defined above, the moiety is referred to herein as a carboxyl group, and particularly when $R^7$ is a hydrogen, the formula represents a "carboxylic acid". Where X is an oxygen, and $R^8$ is a hydrogen, the formula represents a "formate." In general, where the oxygen atom of the above formula is replaced by a sulfur, the formula represents a "thiocarbonyl" group. Where X is a sulfur and $R^7$ or $R^8$ is not hydrogen, the formula represents a "thioester" group. Where X is a sulfur and $R^7$ is a hydrogen, the formula represents a "thiocarboxylic acid" group. Where X is a sulfur and $R^8$ is a hydrogen, the formula represents a "thioformate" group. On the other hand, where X is a bond, and $R^7$ is not hydrogen, the above formula represents a "ketone" group. Where X is a bond, and $R^7$ is a hydrogen, the above formula represents an "aldehyde" group.

The term "thioxamide," as used herein, refers to a moiety that can be represented by the formula:

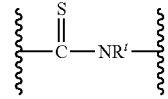

in which $R^t$ is selected from the group consisting of the group consisting of hydrogen, alkyl, cycloalkyl, aralkyl, or aryl, preferably hydrogen or alkyl. Moreover, "thioxamide-derived" compounds or "thioxamide analogs" refer to compounds in which one or more amide groups have been replaced by one or more corresponding thioxamide groups. Thioxamides are also referred to in the art as "thioamides."

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —$NO_2$; the term "halogen" designates —F, —Cl, —Br, or —I; the term "sulfhydryl" means —SH; the term "hydroxyl" means —OH; the term "sulfonyl" means —$SO_2$—; the term "azido" means —$N_3$; the term "cyano" means —CN; the term "isocyanato" means —NCO; the term "thiocyanato" means —SCN; the term "isothiocyanato" means —NCS; and the term "cyanato" means —OCN.

The term "sulfamoyl" is art-recognized and includes a moiety that can be represented by the formula:

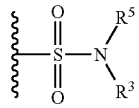

in which $R^3$ and $R^5$ are as defined above.

The term "sulfate" is art recognized and includes a moiety that can be represented by the formula:

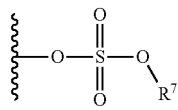

in which $R^7$ is as defined above.

The term "sulfonamide" is art recognized and includes a moiety that can be represented by the formula:

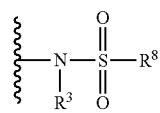

in which $R^3$ and $R^8$ are as defined above.

The term "sulfonate" is art-recognized and includes a moiety that can be represented by the formula:

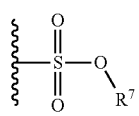

in which $R^7$ is an electron pair, hydrogen, alkyl, cycloalkyl, or aryl.

The terms "sulfoxido" or "sulfinyl", as used herein, refers to a moiety that can be represented by the formula:

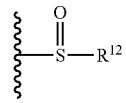

in which $R^{12}$ is selected from the group consisting of the group consisting of hydrogen, alkyl, alkenyl, alkynyl, cycloalkyl, heterocyclyl, aralkyl, or aryl.

As used herein, the definition of each expression, e.g., alkyl, m, n, etc., when it occurs more than once in any structure, is intended to be independent of its definition elsewherein the same structure.

The term "amino acid analog" refers to a compound structurally similar to a naturally occurring amino acid wherein either the C-terminal carboxy group, the N-terminal amino group or side-chain functional group has been chemically modified. For example, aspartic acid-(beta-methyl ester) is an amino acid analog of aspartic acid; N-ethylglycine is an amino acid analog of glycine; or alanine carboxamide is an amino acid analog of alanine.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated, the amino acid or residue can have the configuration (D), (L), or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) and (L) stereoisomers.

The phrase "protecting group" as used herein means substituents which protect the reactive functional group from undesirable chemical reactions. Examples of such protecting groups include esters of carboxylic acids and boronic acids, ethers of alcohols, and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl, and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (Fmoc).

The term "amino-terminal protecting group" as used herein, refers to terminal amino protecting groups that are typically employed in organic synthesis, especially peptide synthesis. Any of the known categories of protecting groups can be employed, including acyl protecting groups, such as acetyl, and benzoyl; aromatic urethane protecting groups, such as benzyloxycarbonyl; and aliphatic urethane protecting groups, such as tert-butoxycarbonyl. See, for example, Gross and Mienhoffer, Eds., *The Peptides*, Academic Press: New York, 1981;, Vol. 3, 3-88; and Green, T. W.; Wuts, P. G. M., *Protective Groups in Organic Synthesis,* 2nd ed, Wiley: New York, 1991. Preferred protecting groups include aryl-, aralkyl-, heteroaryl- and heteroarylalkyl-carbonyl and sulfonyl moieties.

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments where a particular enantiomer is preferred, a compound of the present invention is enriched to have >60%, >70%, >80%, >90%, >95%, or even greater than 98% or 99% of the preferred enantiomer, as opposed to a racemate where the two enantiomers each are present to the extent of 50%.

For purposes of this invention, the chemical elements are identified in accordance with the Periodic Table of the Elements, CAS version, *Handbook of Chemistry and Physics*, 67th ed., 1986-87, inside cover.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the inhibitors of the present invention from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) RingeRs solution; (19) ethyl alcohol; (20) phosphate buffer solutions; and (21) other non-toxic compatible substances employed in pharmaceutical formulations.

The term "pharmaceutically acceptable salts" in these instances refers to the relatively non-toxic, inorganic and organic base addition salts of compounds of the present invention.

The term "pharmaceutically functional derivative" refers to any pharmaceutically acceptable derivative of an inhibitor of the present invention, for example, an ester or an amide, which upon administration to a mammal is capable of providing (directly or indirectly) the inhibitor. Such derivatives are recognizable to those skilled in the art, without undue experimentation. Nevertheless reference is made to the teaching of *Burger's Medicinal Chemistry and Drug Discovery*, 5th ed., Vol 1.

As used herein the term "physiological conditions" refers to temperature, pH, ionic strength, viscosity, and like biochemical parameters which are compatible with a viable organism, and/or which typically exist intracellularly in a viable mammalian cell The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "shelf-life" typically refers to the time period for which the performance characteristics of an inhibitor remain at peak. As used herein, the term "$T_{90}$" refers to the amount of time it takes for a preparation of the subject inhibitor to degrade to the point that it has 90% of the activity of the starting sample, e.g., a diminishment of 10%. Likewise, the term "$T_{50}$" refers to the amount of time it takes for a preparation of the subject inhibitor to degrade to the point that it has 50% of the activity of the starting sample, e.g., a diminishment of 50%. The shelf-life, whether reported as $T_{90}$ or $T_{50}$, for a given pharmaceutical preparation of an inhibitor is the measured for the preparation as it is packaged for use by a healthcare provider or patient.

As used herein the term "substantially soluble" refers to inhibitors which can be dissolved in inhalant propeller mixture to form a substantially clear to hazy solution which will not separate into layers or form a precipitate when left unagitated for a minimum of 24 hours at room temperature.

By "transdermal patch" is meant a system capable of delivery of a drug to a patient via the skin, or any suitable external surface, including mucosal membranes, such as those found inside the mouth. Such delivery systems generally comprise a flexible backing, an adhesive and a drug retaining matrix, the backing protecting the adhesive and matrix and the adhesive holding the whole on the skin of the patient. On contact with the skin, the drug-retaining matrix delivers inhibitor to the skin, the drug then passing through the skin into the patient's system.

The term "quaternizing agent" refers to a chemical compound which converts a nitrogen atom with fewer than four substituents to a positively charged nitrogen atom with four substituents. Examples of "quaternizing agents" include lower alkyl halides, such as methyl, ethyl, propyl, and butyl chloride, bromides, and iodides; dialkyl sulfates like dimethyl, diethyl, dibutyl, and diamyl sulfates, long chain halides, such as decyl, lauryl, myristyl and stearyl chlorides, bromides and iodides, aralkyl halides like benzyl and phenethyl bromides, and others.

Exemplary Embodiments (i). Exemplary Compounds and Salts Thereof

Useful compounds will be described below using various formulae, in most instances. In each case, the variables in the formula are defined specifically for each individual formulae. A definition of a variable for one formula should not be used to vary a definition provided for another formula, although a variable that has not been defined for one formula may be interpreted by analogy with a definition elsewhere for a similar formula.

In certain embodiments, the invention relates to a compound of Formula I:

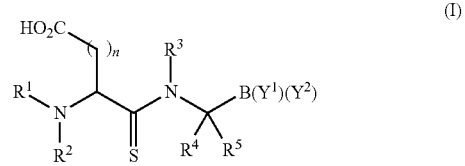

or a pharmaceutically acceptable salt thereof, wherein $R^1$ and $R^2$, independently for each occurrence, represent H, lower alkyl, aralkyl, —C(=O)—OC($R^6$)$_3$, or —C(=O)—C($R^6$)$_3$;

$R^3$ and $R^4$ independently represent H, or alkyl;

$R^5$ represents H, lower alkyl, or aralkyl;

$Y^1$ and $Y^2$ are independently OH, $OR^5$, or a group that is hydrolysable to OH; taken together represent a 1,2-diol or 1,3-diol; or taken together with the boron atom to which they are attached form a 5- to 8-membered ring that is hydrolysable to a boronic acid;

n is an integer from 1 to 4; and $R^6$ is H, alkyl, halo, or aryl.

In certain embodiments, the invention relates to any one of the aforementioned compounds, wherein $R^1$ represents H or lower alkyl.

In certain embodiments, the invention relates to any one of the aforementioned compounds, wherein $R^1$ represents H.

In certain embodiments, the invention relates to any one of the aforementioned compounds, wherein $R^2$ represents H or lower alkyl.

In certain embodiments, the invention relates to any one of the aforementioned compounds, wherein $R^2$ represents H.

In certain embodiments, the invention relates to any one of the aforementioned compounds, wherein $R^3$ represents H or lower alkyl.

In certain embodiments, the invention relates to any one of the aforementioned compounds, wherein $R^3$ represents methyl, ethyl, or propyl.

In certain embodiments, the invention relates to any one of the aforementioned compounds, wherein $R^3$ represents methyl.

In certain embodiments, the invention relates to any one of the aforementioned compounds, wherein $R^4$ represents H or lower alkyl.

In certain embodiments, the invention relates to any one of the aforementioned compounds, wherein $R^4$ represents H.

In certain embodiments, the invention relates to any one of the aforementioned compounds, wherein $R^5$ represents H or lower alkyl.

In certain embodiments, the invention relates to any one of the aforementioned compounds, wherein $R^5$ represents H.

In certain embodiments, the invention relates to any one of the aforementioned compounds, wherein n is 1, 2, or 3.

In certain embodiments, the invention relates to any one of the aforementioned compounds, wherein n is 2.

In certain embodiments, the invention relates to any one of the aforementioned compounds, wherein $Y^1$ is OH.

In certain embodiments, the invention relates to any one of the aforementioned compounds, wherein $Y^2$ is OH.

In certain embodiments, the invention relates to any one of the aforementioned compounds, wherein $Y^1$ is OH; and $Y^2$ is OH.

In certain embodiments, the invention relates to any one of the aforementioned compounds, wherein $Y^1$ and $Y^2$ taken together represent (lower alkyl)CH(OH)CH$_2$CH(OH)(lower alkyl), (lower alkyl)CH(OH)CH(OH)(lower alkyl), HOCH$_2$CH$_2$CH$_2$OH, or HOCH$_2$CH$_2$OH.

In certain embodiments, the invention relates to any one of the aforementioned compounds, wherein $R^1$ is H; $R^2$ is H; $R^3$ is methyl; $R^4$ is H; $R^5$ is H; n is 2; $Y^1$ is OH; and $Y^2$ is OH.

In certain embodiments, the invention relates to a compound of Formula II:

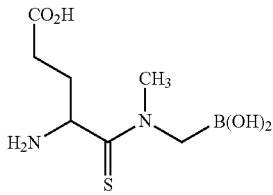

(II)

or a pharmaceutically acceptable salt thereof.

In certain embodiments, the invention relates to a compound of Formula III:

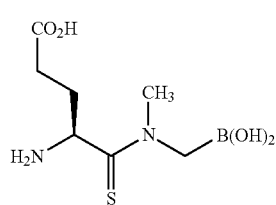

(III)

or a pharmaceutically acceptable salt thereof.

In certain embodiments, the invention relates to any one of the aforementioned compounds, wherein the compounds are DPIV inhibitors with a $K_i$ for DPIV inhibition of about 10 nm or less, about 1.0 nm or less, about 0.1 nM or less, or about 0.01 nM or less. Indeed, inhibitors with $K_i$ values in the picomolar and even femtomolar range are contemplated.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the subject compounds which contain a basic or acid moiety by conventional chemical methods. Generally, the salts are prepared by reacting the free base or acid with stoichiometric amounts or with an excess of the desired salt-forming inorganic or organic acid or base in a suitable solvent. The pharmaceutically acceptable salts of the acids of the subject compounds are also readily prepared by conventional procedures such as treating an acid of the present compounds with an appropriate amount of a base such as an alkali or alkaline earth methyl hydroxide (e.g., sodium, potassium, lithium, calcium or magnesium) or an organic base such as an amine, piperidine, pyrrolidine, benzylamine and the like, or a quaternary ammonium hydroxide such as tetramethylammonium hydroxide and the like.

In certain embodiments, the invention relates to a compound of Formula IV:

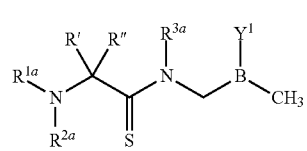

(IV)

or a pharmaceutically acceptable salt thereof, wherein

R' represents H, a lower alkyl which may be unsubstituted or substituted with a hydroxyl, a carboxyl, a halogen, an amine, an amide, a thio, a C1-3 alkylthio, a cycloalkyl, an aryl, an heteroaryl, or a guanidinium group;

R" represents H or a lower alkyl;

$R^{1a}$ represent H, lower alkyl, aralkyl, —C(=O)—OC$(R^6)_3$, —C(=O)—C$(R^6)_3$ a C-terminally linked amino acid or peptide or analog thereof, or an amino protecting group;

$R^{2b}$ represent H, a lower alkyl or taken together with R' a forms a 5, 6 or 7 membered ring;

$R^{3a}$ represents a lower alkyl;

$R^6$ is, independently for each occurrence, H, a lower alkyl, halo, or aryl; and $Y^1$ and $Y^2$ are independently —OH, —OR$^5$, or a group that is hydrolysable to —OH; taken together represent a 1,2-diol or 1,3-diol; or taken together with the boron atom to which they are attached form a 5- to 8-membered ring that is hydrolysable under ordinary physiological conditions to a boronic acid.

In certain embodiments, the invention relates to any one of the aforementioned compounds, where $R^{3a}$ is a methyl.

In certain embodiments, the invention relates to any one of the aforementioned compounds, wherein $Y^1$ and $Y^2$ are —OH.

In certain embodiments, the invention relates to any one of the aforementioned compounds, wherein $R^{1a}$ represents H, or an amino protecting group, and $R^{2b}$ represents H.

In certain embodiments, the invention relates to any one of the aforementioned compounds, wherein R" represents H.

In certain embodiments, the invention relates to any one of the aforementioned compounds, wherein the compound inhibits a post-proline cleaving enzyme with a Ki of 100 nm or less.

In certain embodiments, the invention relates to any one of the aforementioned compounds, wherein the post-proline cleaving enzyme is dipeptidyl peptidase IV (DPP IV). In certain embodiments, the compound of Formula IV is selected from the group consisting of:

Another embodiment of the present invention relates to the use of any one of the aforementioned compounds in the manufacture of a medicament for inhibiting the proteolytic activity of a post-proline-cleaving enzyme in a patient.

In certain embodiments, the invention relates to the use of any one of the aforementioned compounds, wherein the post-proline cleaving enzyme is dipeptidyl peptidase IV (DPP IV).

In certain embodiments, the invention relates to the use of any one of the aforementioned compounds, for the treatment of Type II diabetes, insulin resistance, glucose intolerance, hyperglycemia, hypoglycemia, hyperinsulinemia, obesity, hyperlipidemia, or hyperlipoproteinemia.

In certain embodiments, the invention relates to the use of any one of the aforementioned compounds, for inhibiting cell proliferation associated with tumor growth and metastasis, for inhibiting angiogenesis in an abnormal proliferative cell mass, or both.

Yet another embodiment of the present invention includes methods for inhibiting the proteolytic activity of a post-proline-cleaving enzyme in a patient, comprising administering to a patient in need thereof a therapeutically effective amount of any one of the aforementioned compounds, or a pharmaceutical preparation thereof.

Another embodiment of the present invention includes a compound of any one of the aforementioned claims for use in inhibiting the proteolyic activity of a post-proline-cleaving enzyme in a patient. In certain embodiments, the post-proline cleaving enzyme is dipeptidyl peptidase IV (DPP IV).

Yet another embodiment of the present invention includes a compound of any one of the aforementioned claims for use in the treatment of Type II diabetes, insulin resistance, glucose intolerance, hyperglycemia, hypoglycemia, hyperinsulinemia, obesity, hyperlipidemia, or hyperlipoproteinemia.

Another embodiment of the present invention includes a compound of any one of the aforementioned claims for use in inhibiting cell proliferation associated with tumor growth and metastasis, inhibiting angiogenesis in an abnormal proliferative cell mass, or both.

(ii). Exemplary Prodrug Forms

In certain embodiments, the invention relates to a prodrug form of any one of the aforementioned compounds. In certain embodiments, any one of the aforementioned compounds is a prodrug. These "pro-soft" inhibitors are inactive agents that are activated to release an active inhibitor moiety in proximity to a target protease.

In certain embodiments, the invention relates to a prodrug compound of Formula V:

(V)

wherein $R^1$ represents H, alkyl, alkoxy, alkenyl, alkynyl, amino, alkylamino, acylamino, cyano, sulfonylamino, acyloxy, aryl, cycloalkyl, heterocyclyl, heteroaryl, or a polypeptide chain of 1, 2, 3, 4, 5, 6, 7, or 8 amino acid residues;

$R^2$ represents H, lower alkyl, aralkyl, —C(=O)—OC(R$^8$)$_3$, or —C(=O)—C(R$^8$)$_3$;

$R^3$ and $R^4$ independently represent H or alkyl;

$R^5$ represents H, lower alkyl, or aralkyl;

$Y^1$ and $Y^2$ are independently OH, OR$^5$, or a group that is hydrolysable to OH; taken together represent a 1,2-diol or 1,3-diol; or taken together with the boron atom to which they are attached form a 5- to 8-membered ring that is hydrolysable to a boronic acid;

L is absent or represents alkyl, alkenyl, alkynyl, —(CH$_2$)$_m$O(CH$_2$)$_m$—, —(CH$_2$)$_m$NR$_2$(CH$_2$)$_m$—, and —(CH$_2$)$_m$S(CH$_2$)$_m$—;

X is absent or represents —N(R$^7$)—, —O—, or —S—;

Y is absent or represents —C(=O)—, —C(=S)—, or —SO$_2$—;

R$^7$ represents H, aryl, alkyl, aralkyl, cycloalkyl, heterocyclyl, heteroaryl, heteroaralkyl, or polypeptide chains of 1 to 8 amino acid residues;

R$^8$ is H, alkyl, halo, or aryl;

m is, independently for each occurrence, an integer from 0 to 10; and n is an integer from 1 to 4.

In certain embodiments, the invention relates to a prodrug compound of Formula VI:

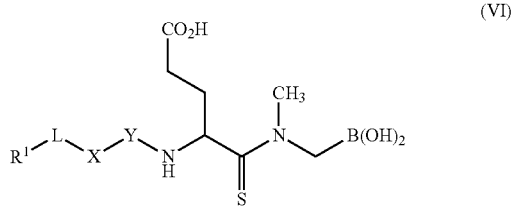

(VI)

or a pharmaceutically acceptable salt thereof,
wherein

R$^1$ represents H, alkyl, alkoxy, alkenyl, alkynyl, amino, alkylamino, acylamino, cyano, sulfonylamino, acyloxy, aryl, cycloalkyl, heterocyclyl, heteroaryl, or a polypeptide chain of 1, 2, 3, 4, 5, 6, 7, or 8 amino acid residues;

L is absent or represents alkyl, alkenyl, alkynyl, —(CH$_2$)$_m$O(CH$_2$)$_m$—, —(CH$_2$)$_m$NR$_2$(CH$_2$)$_m$—, and —(CH$_2$)$_m$S(CH$_2$)$_m$—;

X is absent or represents —N(R$^7$)—, —O—, or —S—;

Y is absent or represents —C(=O)—, —C(=S)—, or —SO$_2$—;

m is, independently for each occurrence, an integer from 0 to 10; and

R$^7$ represents H, aryl, alkyl, aralkyl, cycloalkyl, heterocyclyl, heteroaryl, heteroaralkyl, or polypeptide chains of 1 to 8 amino acid residues.

In certain embodiments, the invention relates to a prodrug compound of Formula VII:

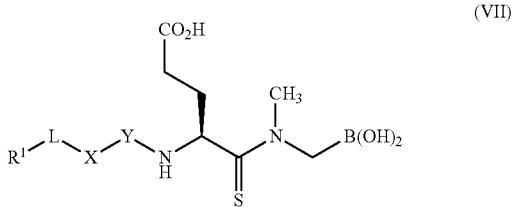

(VII)

or a pharmaceutically acceptable salt thereof
wherein

R$^1$ represents H, alkyl, alkoxy, alkenyl, alkynyl, amino, alkylamino, acylamino, cyano, sulfonylamino, acyloxy, aryl, cycloalkyl, heterocyclyl, heteroaryl, or a polypeptide chain of 1, 2, 3, 4, 5, 6, 7, or 8 amino acid residues;

L is absent or represents alkyl, alkenyl, alkynyl, —(CH$_2$)$_m$O(CH$_2$)$_m$—, —(CH$_2$)$_m$NR$_2$(CH$_2$)$_m$—, and —(CH$_2$)$_m$S(CH$_2$)$_m$—;

X is absent or represents —N(R$^7$)—, —O—, or —S—;

Y is absent or represents —C(=O)—, —C(=S)—, or —SO$_2$—;

m is, independently for each occurrence, an integer from 0 to 10; and

R$^7$ represents H, aryl, alkyl, aralkyl, cycloalkyl, heterocyclyl, heteroaryl, heteroaralkyl, or polypeptide chains of 1 to 8 amino acid residues.

In certain embodiments, the invention relates to any one of the aforementioned prodrug compounds, wherein R$^2$ represents H or lower alkyl.

In certain embodiments, the invention relates to any one of the aforementioned prodrug compounds, wherein R$^2$ represents H.

In certain embodiments, the invention relates to any one of the aforementioned prodrug compounds, wherein R$^3$ represents H or lower alkyl.

In certain embodiments, the invention relates to any one of the aforementioned prodrug compounds, wherein R$^3$ represents methyl, ethyl, or propyl.

In certain embodiments, the invention relates to any one of the aforementioned prodrug compounds, wherein R$^3$ represents methyl.

In certain embodiments, the invention relates to any one of the aforementioned prodrug compounds, wherein R$^4$ represents H or lower alkyl.

In certain embodiments, the invention relates to any one of the aforementioned prodrug compounds, wherein R$^4$ represents H.

In certain embodiments, the invention relates to any one of the aforementioned prodrug compounds, wherein R$^5$ represents H or lower alkyl.

In certain embodiments, the invention relates to any one of the aforementioned prodrug compounds, wherein R$^5$ represents H.

In certain embodiments, the invention relates to any one of the aforementioned prodrug compounds, wherein n is 1, 2, or 3.

In certain embodiments, the invention relates to any one of the aforementioned prodrug compounds, wherein n is 2.

In certain embodiments, the invention relates to any one of the aforementioned prodrug compounds, wherein Y$^1$ is OH.

In certain embodiments, the invention relates to any one of the aforementioned prodrug compounds, wherein Y$^2$ is OH.

In certain embodiments, the invention relates to any one of the aforementioned prodrug compounds, wherein Y$^1$ is OH; and Y$^2$ is OH.

In certain embodiments, the invention relates to any one of the aforementioned prodrug compounds, wherein Y$^1$ and Y$^2$ taken together represent (lower alkyl)CH(OH)CH$_2$CH(OH)(lower alkyl), (lower alkyl)CH(OH)CH(OH)(lower alkyl), HOCH$_2$CH$_2$CH$_2$OH, or HOCH$_2$CH$_2$OH.

In certain embodiments, the invention relates to any one of the aforementioned prodrug compounds, wherein L is absent.

In certain embodiments, the invention relates to any one of the aforementioned prodrug compounds, wherein X is absent.

In certain embodiments, the invention relates to any one of the aforementioned prodrug compounds, wherein Y is absent.

In certain embodiments, the invention relates to any one of the aforementioned prodrug compounds, wherein R$^1$ is a polypeptide chain of 2, 3, 4, 5, 6, 7, or 8 amino acid residues.

In certain embodiments, the invention relates to any one of the aforementioned prodrug compounds, wherein R$^1$ is a polypeptide chain of 2, 3, 4, 5, 6, 7, or 8 amino acid residues; and proline is the amino acid residue directly attached to L.

In certain embodiments, the invention relates to any one of the aforementioned prodrug compounds, wherein R$^1$ is a polypeptide chain of 2 amino acid residues.

In certain embodiments, the invention relates to any one of the aforementioned prodrug compounds, wherein $R^1$ is a polypeptide chain of 2 amino acid residues; and proline is the amino acid residue directly attached to L.

In certain embodiments, the invention relates to any one of the aforementioned prodrug compounds, wherein $R^1$ is a polypeptide chain of 2 amino acid residues; L is absent; X is absent; Y is absent; and proline is the amino acid residue directly attached to N.

In certain embodiments, the invention relates to any one of the aforementioned prodrug compounds, wherein $R^2$ represents H; $R^3$ represents methyl; $R^4$ represents H; $R^5$ represents H; n is 2; $Y^1$ is OH; $Y^2$ is OH; L is absent; X is absent; Y is absent; and $R^1$ is a polypeptide chain of 2 amino acid residues.

In certain embodiments, the invention relates to any one of the aforementioned prodrug compounds, wherein $R^2$ represents H; $R^3$ represents methyl; $R^4$ represents H; $R^5$ represents H; n is 2; $Y^1$ is OH; $Y^2$ is OH; L is absent; X is absent; Y is absent; $R^1$ is a polypeptide chain of 2 amino acid residues; and proline is the amino acid residue directly attached to N.

In certain embodiments, the invention relates to any one of the aforementioned prodrug compounds, wherein the activating protease is a serine protease, a cysteine protease, or a metalloprotease. In certain embodiments, the invention relates to any one of the aforementioned prodrug compounds, wherein the target protease is a serine protease, a cysteine protease, or a metalloprotease. In certain embodiments, the invention relates to any one of the aforementioned prodrug compounds, wherein the target and activating proteases are serine proteases.

In certain embodiments, the invention relates to any one of the aforementioned prodrug compounds, wherein the activating protease is a post-prolyl cleaving protease. In certain embodiments, the invention relates to any one of the aforementioned prodrug compounds, wherein the activating protease is selected from the group consisting of DPP IV, DPP II, Prolyl oligopeptidase (PO), Fibroblast Activating Protein (FAP), and prolyl carboxypeptidase. In certain embodiments, the invention relates to any one of the aforementioned prodrug compounds, wherein the post-prolyl cleaving protease is an endopeptidase, and A comprises a blocked amino terminus.

In certain embodiments, the invention relates to any one of the aforementioned prodrug compounds, wherein the activating protease is selected from the group consisting of thrombin (Factor X), matriptase, falcipain, prostate specific antigen (PSA), and proteases homologous thereto.

In certain embodiments, the invention relates to any one of the aforementioned prodrug compounds, wherein the inhibitor is activated by a fibroblast activating protein to release a compound that inhibits prostate specific antigen (PSA).

In certain embodiments, the invention relates to any one of the aforementioned prodrug compounds, wherein the inhibitor is activated by a PSA to release a compound that inhibits proteasome activity.

In certain embodiments, the invention relates to any one of the aforementioned prodrug compounds, wherein the target protease is a post-prolyl cleaving protease. In certain embodiments, the invention relates to any one of the aforementioned prodrug compounds, wherein the target protease is selected from the group consisting of DPP IV, DPP II, Prolyl oligopeptidase (PO), Fibroblast Activating Protein (FAP), and prolyl carboxypeptidase.

One of the features that makes the pro-soft inhibitor molecules of the current invention different from typical prodrugs is that, in certain embodiments of the invention, the inhibitor moiety, after being generated in the active form near the target, undergoes inactivation over time, e.g., as it diffuses away from the target enzyme, thereby reducing the possibility of deleterious side effects that may result from inhibition of enzymes occurring in other parts of the patient. This combination of being released in an active form in the vicinity of the target enzyme together with this "programmed" deactivation mechanism makes the molecules of the invention more specific, effective, and safer (i.e., having fewer side effects) than the inhibitor moiety used on its own.

In certain embodiments, the invention relates to any one of the aforementioned prodrug compounds, wherein the therapeutic index for the pro-soft inhibitor is at least about 2 times greater than the therapeutic index for the inhibitor moiety alone, at least about 5 times greater, at least about 10 times greater, at least about 50 times greater, or at least about 100 times greater.

For many of the subject pro-soft inhibitors, another improvement over the inhibitor moiety itself is increased stability in pharmaceutical preparations, such as in solution, oils or solid formulations. Such stability can be expressed in terms of shelf-life. In certain embodiments, the invention relates to any one of the aforementioned prodrug compounds, wherein the subject pro-soft inhibitor has a $T_{90}$ of at least about 7 days, at least about 20 days, at least about 50 days, at least about 100 days, or at least about 200 days. In certain embodiments, the invention relates to any one of the aforementioned prodrug compounds, wherein the subject pro-soft inhibitor has a $T_{50}$ of at least about 20 days, at least about 50, at least about 100, at least about 200, or at least about 400 days. In certain embodiments, the invention relates to any one of the aforementioned prodrug compounds, wherein the subject pro-soft inhibitor has a $T_{90}$ as a solid, single oral dosage formulation of at least about 20, at least about 50, at least about 100, or at least about 200 days. In certain embodiments, the invention relates to any one of the aforementioned prodrug compounds, wherein the subject pro-soft inhibitor has a $T_{90}$ as a liquid, single dosage suspension of at least about 20, at least about 50, at least about 100, or at least about 200 days.

In certain embodiments, the invention relates to any one of the aforementioned prodrug compounds, wherein the pro-soft inhibitor comprises one or more chiral centers. In certain embodiments, the invention relates to any one of the aforementioned prodrug compounds, wherein the pro-soft inhibitor is provided as from at least about 75 mol % of the eutomer (relative to the distomer) of that pro-soft inhibitor, to about 99.999 mol % of the eutomer. In certain embodiments, the invention relates to any one of the aforementioned prodrug compounds, wherein the pro-soft inhibitor is provided as from at least about 85, at least about 90, at least about 95, or at least about 99 mol %, to about 99.999 mol % of the eutomer. In certain embodiments, the invention relates to any one of the aforementioned prodrug compounds, wherein the pro-soft inhibitor is the eutomer with the L-enantiomer (with respect to the Cα carbon) of an amino acid or amino acid analog.

In general, the subject pro-soft inhibitors can be divided into two distinct types on the basis of whether they are activated by the same, or by a different enzyme as the target enzyme of the inhibitor moiety. The first type will be referred to as Type 1 or Target-Activated Smart Protease Inhibitors (TASPI), the second as Type 2 or Target-Directed Smart Protease Inhibitors (TDSPI). Both embodiments of the pro-soft inhibitors provide for the specific delivery of the active component to the targeted enzyme and provide for attenuation of the inhibitor activity as the inhibitor moiety diffuses away from the target enzyme.

In certain embodiments, the invention relates to any one of the aforementioned TDSPIs, wherein the TDSPI offers the additional prospects for tissue, or cellular specific inhibition of targeted enzymes. In certain embodiments, the invention relates to any one of the aforementioned TDSPIs, wherein the TDSPI offers the prospect of inhibiting a given enzyme in one given cell or tissue type but not in another. For example, every cell of the body contains a proteasome protease complex. Inhibition of proteasome function has a number of practical therapeutic and prophylactic applications. However, it is difficult to provide for inhibition of proteasome activity in a cell- or tissue-type selective manner. In certain embodiments, the invention relates to any one of the aforementioned TDSPIs, wherein the TDSPI can be constructed to deliver a proteasome inhibitor moiety in selective manner by using a pro-soft inhibitor having an address moiety for a protease that is expressed in or adjacent to the intended target cells or tissue. In certain embodiments, the invention relates to any one of the aforementioned TDSPIs, wherein the TDSPI can be activated by FAP or Prostate Specific Antigen (PSA) and the resulting inhibitor moiety G is an inhibitor of the proteasome.

In certain embodiments, the invention relates to any one of the aforementioned prodrug compounds, wherein the address moiety is a substrate for an activating protease selected from the group consisting of serine proteases, cysteine proteases, and metalloproteases. In certain embodiments, the invention relates to any one of the aforementioned prodrug compounds, wherein the inhibitor moiety is dipeptidyl inhibitor for a target protease selected from the group consisting of serine proteases, cysteine proteases, and metalloproteases. In certain embodiments, the invention relates to any one of the aforementioned prodrug compounds, wherein the target protease is a serine protease.

In certain embodiments, the invention relates to any one of the aforementioned prodrug compounds, wherein the pro-soft inhibitors can be designed to work with target and activating serine proteases including, but not limited to, dipeptidyl peptidase-11 (DPP-XI), dipeptidyl peptidase IV (DPP IV), dipeptidyl peptidase (DPP VIII), dipeptidyl peptidase 9 (DPP IX), aminopeptidase P, fibroblast activating protein alpha (seprase), prolyl tripeptidyl peptidase, prolyl oligopeptidase (endoproteinase Pro-C), attractin (soluble dipeptidyl-aminopeptidase), acylaminoacyl-peptidase (N-acylpeptide hydrolase; fMet aminopeptidase) and lysosomal Pro-X carboxypeptidase (angiotensinase C, prolyl carboxypeptidase).

In certain embodiments, the invention relates to any one of the aforementioned prodrug compounds, wherein the pro-soft inhibitors can be designed to work with target and activating metalloproteases including, but not limited to, membrane Pro-X carboxypeptidase (carboxypeptidase P), angiotensin-converting enzyme (Peptidyl-dipeptidase A multipeptidase], collagenase I (interstitial collagenase; matrix metalloproteinase 1; MMP-1; Mcol-A), ADAM 10 (alpha-secretase, myelin-associated disintegrin metalloproteinase), neprilysin (atriopeptidase; CALLA; CD10; endopeptidase 24.1 1; enkephalinase), Macrophage elastase (metalloelastase; matrix metalloproteinase 12; MMP-12], Matrilysin (matrix metalloproteinase 7; MMP-7), and neurolysin (endopeptidase 24.16; microsomal endopeptidase; mitochondrial oligopeptidase).

In certain embodiments, the invention relates to any one of the aforementioned prodrug compounds, wherein the activating protease is a post-prolyl cleaving protease. In certain embodiments, the invention relates to any one of the aforementioned prodrug compounds, wherein the activating protease selected from the group consisting of DPP IV, DPP II, Prolyl oligopeptidase (PO), Fibroblast Activating Protein (FAP), and prolyl carboxypeptidase.

In certain embodiments, the invention relates to any one of the aforementioned prodrug compounds, wherein the pro-soft inhibitor is activated by one protease and inhibits a different protease.

Also included are such peptidomimetics as olefins, phosphonates, aza-amino acid analogs and the like.

Contemplated equivalents of the compounds described above include compounds which otherwise correspond thereto, and which have the same general properties thereof (e.g., the ability to inhibit proteolysis of GLP-1 or other peptide hormone or precursor thereof), wherein one or more simple variations of substituents are made which do not adversely affect the efficacy of the compound in use in the contemplated method. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

(iii). Agonism of GLP-1 Effects

The compounds useful in the subject methods possess, in certain embodiments, the ability to lower blood glucose levels, to relieve obesity, to alleviate impaired glucose tolerance, to inhibit hepatic glucose neogenesis, and to lower blood lipid levels and to inhibit aldose reductase. They are thus useful for the prevention and/or therapy of hyperglycemia, obesity, hyperlipidemia, diabetic complications (including retinopathy, nephropathy, neuropathy, cataracts, coronary artery disease and arteriosclerosis), and furthermore for obesity-related hypertension and osteoporosis.

Diabetes mellitus is a disease characterized by hyperglycemia occurring from a relative or absolute decrease in insulin secretion, decreased insulin sensitivity, or insulin resistance. The morbidity and mortality of this disease result from vascular, renal, and neurological complications. An oral glucose tolerance test is a clinical test used to diagnose diabetes. In an oral glucose tolerance test, a patient's physiological response to a glucose load or challenge is evaluated. After ingesting the glucose, the patient's physiological response to the glucose challenge is evaluated. Generally, this is accomplished by determining the patient's blood glucose levels (the concentration of glucose in the patient's plasma, serum, or whole blood) for several predetermined points in time.

In one embodiment, the present invention provides a method for agonizing the action of GLP-1. It has been determined that isoforms of GLP-1 (GLP-1 (7-37) and GLP-1 (7-36)), which are derived from preproglucagon in the intestine and the hind brain, have insulinotropic activity, i.e., they modulate glucose metabolism. DPIV cleaves the isoforms to inactive peptides. Thus, in certain embodiments, compound(s) of the present invention can agonize insulinotropic activity by interfering with the degradation of bioactive GLP-1 peptides.

In certain embodiments, the method involves administration of a DPIV inhibitor in an amount effective to improve aberrant indices associated with obesity. Fat cells release the hormone leptin, which travels in the bloodstream to the brain and, through leptin receptors there, stimulates production of GLP-1. GLP-1, in turn, produces the sensation of being full. The leading theory is that the fat cells of most obese people probably produce enough leptin, but leptin may not be able to properly engage the leptin receptors in the brain, and so does not stimulate production of GLP-1. There is accordingly a great deal of research towards utilizing preparations of GLP-1 as an appetite suppressant. The subject method provides a means for increasing the half-life of both endogenous and ectopically added GLP-1 in the treatment of disorders associated with obesity.

(iv). Agonism of the Effects of Other Peptide Hormones

In another embodiment, the subject agents can be used to agonize (e.g., mimic or potentiate) the activity of peptide hormones, e.g., GLP-2, GIP and NPY.

In certain embodiments, the present invention provides methods and compositions for altering the pharmacokinetics of a variety of different polypeptide hormones by inhibiting the proteolysis of one or more peptide hormones by DPIV or some other proteolytic activity. Post-secretory metabolism is an important element in the overall homeostasis of regulatory peptides, and the other enzymes involved in these processes may be suitable targets for pharmacological intervention by the subject method.

In certain embodiments, the subject method can be used to increase the half-life of other proglucagon-derived peptides, such as glicentin (corresponding to PG 1-69), oxyntomodulin (PG 33-69), glicentin-related pancreatic polypeptide (GRPP, PG 1-30), intervening peptide-2 (IP-2, PG 111-122amide), and glucagon-like peptide-2 (LPD-2, PG 126-158). For example, glicentin has been demonstrated to cause proliferation of intestinal mucosa and also inhibits a peristalsis of the stomach, and has thus been elucidated as useful as a therapeutic agent for digestive tract diseases, thus leading to the present invention.

To illustrate further, the present invention provides a method for agonizing the action of GLP-2. It has been determined that GLP-2 acts as a trophic agent, to promote growth of gastrointestinal tissue. The effect of GLP-2 is marked particularly by increased growth of the small bowel, and is therefore herein referred to as an "intestinotrophic" effect. DPIV is known to cleave GLP-2 into a biologically inactive peptide. Thus, in one embodiment, inhibition of DPIV interferes with the degradation of GLP-2, and thereby increases the plasma half-life of that hormone. In certain embodiments, the invention relates to a method for treating injury, inflammation, or resection of intestinal tissue, e.g., where enhanced growth and repair of the intestinal mucosal epithelial is desired, such as in the treatment of Crohn's disease or Inflammatory Bowel Disease (IBD).

Thus, in one aspect, the present invention relates to therapeutic and related uses of compound(s) for promoting the growth and proliferation of gastrointestinal tissue, most particularly small bowel tissue. For instance, the subject method can be used as part of a regimen for treating injury, inflammation, or resection of intestinal tissue, e.g., where enhanced growth and repair of the intestinal mucosal epithelial is desired.

In general, patients who would benefit from either increased small intestinal mass and consequent increased small bowel mucosal function are candidates for treatment by the subject method.

More generally, the present invention provides a therapeutic method for treating digestive tract diseases. The subject method, because of promoting proliferation of intestinal mucosa, can be used in the treatment and prevention of pathologic conditions of insufficiency in digestion and absorption, that is, treatment and prevention of mucosal atrophy, or treatment of hypoplasia of the digestive tract tissues and decrease in these tissues by surgical removal as well as improvement of digestion and absorption. Further, the subject method can be used in the treatment of pathologic mucosal conditions due to inflammatory diseases such as enteritis, Crohn's disease, and ulceric colitis and also in the treatment of reduction in function of the digestive tract after operation. Furthermore, glicentin can effectively be used in promoting cure of surgical invasion as well as in improving functions of the digestive tract. Thus, the present invention also provides a therapeutic agent for atrophy of the digestive tract mucosa, a therapeutic agent for wounds in the digestive tract and a drug for improving functions of the digestive tract which comprise glicentin as active ingredients.

Likewise, the compound(s) of the subject invention can be used to alter the plasma half-life of secretin, VIP, PHI, PACAP, GIP, and/or helodermin. Additionally, the subject method can be used to alter the pharmacokinetics of Peptide YY and neuropeptide Y, both members of the pancreatic polypeptide family, as DPIV has been implicated in the processing of those peptides in a manner which alters receptor selectivity.

Neuropeptide Y (NPY) is believed to act in the regulation vascular smooth muscle tone, as well as regulation of blood pressure. NPY also decreases cardiac contractility. NPY is also the most powerful appetite stimulant known (Wilding et al., *J. Endocrinology* 1992, 132, 299-302). The centrally evoked food intake (appetite stimulation) effect is predominantly mediated by NPY Y1 receptors and causes increase in body fat stores and obesity (Stanley et al., *Physiology and Behavior* 1989, 46, 173-177).

According to the present invention, a method for treatment of anorexia comprises administering to a host subject an effective amount of a compound(s) to stimulate the appetite and increase body fat stores which thereby substantially relieves the symptoms of anorexia.

In certain embodiments, the invention relates to a method of regulating body fat or lipid stores.

DPIV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP), and helodermin (Kubiak et al. *Peptide Res.* 1994, 7, 153). GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

(v). Hematopoietic Agonists

In still another aspect, the present invention provides a method for stimulating hematopoietic cells in culture or in vivo. In certain embodiments, the subject DPP IV pro-inhibitors include an address moiety that is a substrate for a protease that is expressed in bone marrow.

According to one aspect of the invention, a method for stimulating hematopoietic cells in vitro is provided. The method involves (1) contacting the hematopoietic cells with a sufficient amount of an DPP IV pro-inhibitor to increase the number of hematopoietic cells and/or the differentiation of such hematopoietic cells relative to the number and differentiation of hematopoietic cells.

In certain embodiments, the compounds can be used to inhibit growth or vascularization of transformed cells/tissues, e.g., to inhibit cell proliferation such as that associated with tumor growth and metastasis, and for inhibiting angiogenesis in an abnormal proliferative cell mass. In yet other embodiments, the compounds can be used to reduce immunological responses, e.g., as an immunosuppressant.

One important aspect of the invention involves restoring or preventing a deficiency in hematopoietic cell number in a subject. Such deficiencies can arise, for example, from genetic abnormalities, from disease, from stress, from chemotherapy (e.g. cytotoxic drug treatment, steroid drug treatment, immunosuppressive drug treatment, etc.) and from radiation treatment.

Thus, it is known that interleukins-1, 2, 3, 4, 5, 6, 7, 9, 10, 11, 12, 13, and 17 are involved in lymphocyte differentiation. Interleukins 3 and 4 are involved in mast cell differentiation. Granulocyte macrophage colony stimulating factor (GMCSF), interleukin-3 and interleukin-5 are involved in the eosinophil differentiation. GMCSF, macrophage colony stimulating factor (MCSF) and IL-3 are involved in macrophage differentiation.

GMCSF, GCSF and IL-3 are involved in neutrophil differentiation. GMSCF, IL-3, IL-6, IL-11 and TPO are involved in platelet differentiation. Flt3 Ligand is involved in dendritic cell growth. GMCSF, IL-3, and erythropoietin are involved in erythrocyte differentiation.

Finally, the self-renewal of primitive, pluripotent progenitor cells capable of sustaining hematopoiesis requires SCF, Flt3 Ligand, G-CSF, IL-3, IL-6 and IL-11. Various combinations for achieving a desired result will be apparent to those of ordinary skill in the art.

(vi). Conjoint Administration

Another aspect of the invention provides a conjoint therapy wherein one or more other therapeutic agents are administered with the compound. Such conjoint treatment may be achieved by way of the simultaneous, sequential, or separate dosing of the individual components of the treatment.

A large number of pharmaceutical agents or therapeutic agents are known in the art and are amenable for use in the pharmaceutical compositions of the invention. The term "pharmaceutical agent" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

In one embodiment, a compound(s) is conjointly administered with insulin or other insulinotropic agents, such as GLP-1, peptide hormones, such as GLP-2, GIP, or NPY, or a gene therapy vector which causes the ectopic expression of said agents and peptide hormones. In certain embodiments, said agents or peptide hormones may be variants of a naturally occurring or synthetic peptide hormone, wherein one or more amino acids have been added, deleted, or substituted.

In another illustrative embodiment, the compounds can be conjointly administered with an M1 receptor antagonist. Cholinergic agents are potent modulators of insulin release that act via muscarinic receptors. Moreover, the use of such agents can have the added benefit of decreasing cholesterol levels, while increasing HDL levels. Suitable muscarinic receptor antagonists include substances that directly or indirectly block activation of muscarinic cholinergic receptors. Preferably, such substances are selective (or are used in amounts that promote such selectivity) for the M1 receptor. Non-limiting examples include quaternary amines (such as methantheline, ipratropium, and propantheline), tertiary amines (e.g., dicyclomine and scopolamine), and tricyclic amines (e.g., telenzepine). Pirenzepine and methyl scopolamine are preferred. Other suitable muscarinic receptor antagonists include benztropine (commercially available as COGENTIN from Merck), hexahydro-sila-difenidol hydrochloride (HHSID hydrochloride disclosed in Lambrecht et al. *Trends in Pharmacol. Sci.* 1989, 10(Suppl), 60; (+/−)-3-quinuclidinyl xanthene-9-carboxylate hemioxalate (QNX-hemioxalate; Birdsall et al., *Trends in Pharmacol. Sci.* 1983, 4, 459; telenzepine dihydrochloride (Coruzzi et al. *Arch. Int. Pharmacodyn. Ther.* 1989, 302, 232; and Kawashima et al. *Gen. Pharmacol.* 1990, 21, 17), and atropine. The dosages of such muscarinic receptor antagonists will be generally subject to optimization as outlined above. In the case of lipid metabolism disorders, dosage optimization may be necessary independent of whether administration is timed by reference to the lipid metabolism responsiveness window or not.

In terms of regulating insulin and lipid metabolism and reducing the foregoing disorders, the compound(s) may also act synergistically with prolactin inhibitors such as d2 dopamine agonists (e.g., bromocriptine). Accordingly, the subject method can include the conjoint administration of such prolactin inhibitors as prolactin-inhibiting ergo alkaloids and prolactin-inhibiting dopamine agonists. Examples of suitable compounds include 2-bromo-alpha-ergocriptine, 6-methyl-8-beta-carbobenzyloxyaminoethyl-10-alpha-ergoline, 8-acylaminoergolines, 6-methyl-8-alpha-(N-acyl) amino-9-ergoline, 6-methyl-8-alpha-(N-phenylacetyl) amino-9-ergoline, ergocornine, 9,10-dihydroergocornine, D-2-halo-6-alkyl-8-substituted ergolines, D-2-bromo-6-methyl-8-cyanomethylergoline, carbidopa, benserazide, and other dopadecarboxylase inhibitors, L-dopa, dopamine, and non toxic salts thereof.

The compound(s) used according to the invention can also be used conjointly with agents acting on the ATP-dependent potassium channel of the β-cells, such as glibenclamide, glipizide, gliclazide, and AG-EE 623 ZW. The compound(s) may also advantageously be applied in combination with other oral agents such as metformin and related compounds or glucosidase inhibitors as, for example, acarbose.

(vii). Pharmaceutical Compositions

In certain embodiments, the invention relates to a pharmaceutical composition comprising a pharmaceutically acceptable carrier; and any of the aforementioned compounds or a pharmaceutically acceptable salt thereof.

While it is possible for a compound of the present invention to be administered alone, in certain cases it is preferable to administer the compound as a pharmaceutical formulation (composition). Protease inhibitors, and prodrug forms thereof, according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

In certain embodiments, the invention relates to a pharmaceutical composition comprising any one of the aforementioned compounds. In certain embodiments, the invention relates to any one of the aforementioned compositions, wherein the composition is formulated for oral, buccal, parental, transdermal, inhalation, intranasal, transmucosal, implant, or rectal administration. In certain embodiments, the invention relates to any one of the aforementioned compositions, wherein the subject inhibitor is orally available, and can be provided in the form of solid dosage compositions suitable for oral administration to a human patient. In certain embodiments, the invention relates to any one of the aforementioned compositions, wherein the subject inhibitor is transdermally active, and can be provided in the form of topical cream or suspension or a transdermal patch.

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent, or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the compound that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound(s) with the carrier and, optionally, one or more accessory ingredients. In general, the formulations are prepared by uniformly and intimately bringing into association a ligand with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes, and the like, each containing a predetermined amount of a compound(s) as an active ingredient. A compound may also be administered as a bolus, electuary or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compound(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of a compound(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to compound(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The compound(s) can be alternatively administered by aerosol. This is accomplished by preparing an aqueous aerosol, liposomal preparation, or solid particles containing the compound. A non-aqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Medicaments which may be administered in inhalant or aerosol formulations according to the invention include protease inhibitor prodrugs useful in inhalation therapy which may be presented in a form which is soluble or substantially soluble in the selected propellant system.

The particle size of the particulate medicament should be such as to permit inhalation of substantially all of the medicament into the lungs upon administration of the aerosol formulation and will thus desirably be less than 20 microns, preferably in the range 1 to 10 microns, e.g., 1 to 5 microns. The particle size of the medicament may be reduced by conventional means, for example by milling or micronisation.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time. Preferably, administration may be one time per day.

For administration, the drug is suitably inhaled from a nebulizer, from a pressurized metered dose inhaler, or as a dry powder from a dry powder inhaler (e.g., sold as TURBU-HALER®) or from a dry powder inhaler utilizing gelatin, plastic or other capsules, cartridges or blister packs.

A diluent or carrier, generally non-toxic and chemically inert to the medicament; e.g., lactose, dextran, mannitol, glucose or any additives that will give the medicament a desired taste, can be added to the powdered medicament.

The micronized mixture may be suspended or dissolved in a liquid propellant mixture which is kept in a container that is sealed with a metering valve and fitted into a plastic actuator. The propellants used may be halocarbons of different chemical formulae. The most frequently used halocarbon propellants are trichlorofluoromethane, dichlorodifluoromethane, dichlorotetrafluoroethane, tetrafluoroethane, and 1,1-difluoroethane. Low concentrations of a surfactant such as sorbitan trioleate, lecithin, disodium dioctylsulphosuccinate, or oleic acid may also be used to improve the physical stability.

Transdermal patches have the added advantage of providing controlled delivery of a compound(s) to the body. Such dosage forms can be made by dissolving or dispersing the agent in the proper medium. Absorption enhancers can also be used to increase the flux of the compound(s) across the skin. The rate of such flux can be controlled by either providing a rate controlling membrane or dispersing the peptidomimetic in a polymer matrix or gel.

Ophthalmic formulations, eye ointments, powders, solutions, and the like, are also contemplated as being within the scope of this invention.

Pharmaceutical compositions of this invention suitable for parenteral administration comprise one or more compounds(s) in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of compound(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds(s) of the present invention are administered as pharmaceuticals to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These compounds(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as *Applied Animal Nutrition*; San Francisco: Freedman, 1969; or *Livestock Feeds and Feeding*; Corvallis: O & B Books, 1977).

Regardless of the route of administration selected, the compound(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

(viii). Pharmaceutical Packages and Manufacture

In certain embodiments, the invention relatest to a packaged pharmaceutical, comprising any one of the aforementioned compounds; and instructions for use thereof.

In certain embodiments, the invention relatest to a packaged pharmaceutical comprising one or more inhibitors of the present invention formulated in a pharmaceutically acceptable excipient, in association with instructions (written and/or pictorial) describing the recommended dosage and/or administration of the formulation to a patient. Such instructions may include details for treating or preventing a diseases, and optionally, warnings of possible side effects and drug-drug or drug-food interactions.

Yet another aspect of the invention relates to a method for conducting a pharmaceutical business, which includes:

a. manufacturing one or more of the subject inhibitors; and b. marketing to healthcare providers the benefits of using the preparation to treat or prevent any of the diseases or indications cited herein.

In certain embodiments, the subject business method can include providing a distribution network for selling the preparation. It may also include providing instruction material to patients or physicians for using the preparation to treat and prevent any of the diseases or indications cited herein.

In certain embodiments, the invention relates to any one of the aforementioned packaged pharmaceuticals, wherein said instructions relate to use in regulation of glucose metabolism or inhibition of a post-proline-cleaving enzyme.

In certain embodiments, the invention relates to any one of the aforementioned packaged pharmaceuticals, wherein said instructions relate to use in inhibition of a proteasome, DP8, DP9, or prostate-specific antigen.

In certain embodiments, the invention relates to any one of the aforementioned packaged pharmaceuticals, wherein the compound is co-formulated with or co-packaged with insulin, an insulinotropic agent or both.

In certain embodiments, the invention relates to any one of the aforementioned packaged pharmaceuticals, wherein the compound is co-formulated with or co-packaged with an M1 receptor antagonist, a prolactin inhibitor, an agent acting on the ATP-dependent potassium channel of β-cells, metformin, a glucosidase inhibitor or a combination of any of them.

(ix). Exemplary Methods of the Invention

In certain embodiments, the invention relates to a method for inhibiting the proteolytic activity of a post-proline-cleaving enzyme, comprising contacting said enzyme with any one of the aforementioned compounds.

In certain embodiments, the invention relates to any one of the aforementioned methods, wherein said enzyme is a mammalian dipeptidyl peptidase IV (DPP IV).

In certain embodiments, the invention relates to a method for inhibiting the proteolytic activity of a post-proline-cleaving enzyme in a patient, comprising administering to a patient in need thereof a therapeutically effective amount of any one of the aforementioned compounds.

In certain embodiments, the invention relatest to any one of the aforementioned methods, wherein the method increases the patient's plasma concentrations of a peptide hormone selected from the group consisting of glucagon-like peptide, NPY, PPY, secretin, GLP-1, GLP-2, and GIP.

In certain embodiments, the invention relates to a method of regulating glucose metabolism in a patient, comprising administering to a patient in need thereof a therapeutically effective amount of any one of the aforementioned compounds.

In certain embodiments, the invention relatest to any one of the aforementioned methods, wherein the patient is suffering from Type II diabetes, insulin resistance, glucose intolerance, hyperglycemia, hypoglycemia, hyperinsulinemia, obesity, hyperlipidemia, or hyperlipoproteinemia (such as chylomicrons, VLDL and LDL).

In certain embodiments, the invention relatest to any one of the aforementioned methods, further comprising administering to said patient a therapeutically effective amount of insulin, an insulinotropic agent or both.

In certain embodiments, the invention relatest to any one of the aforementioned methods, further comprising administering to said patient a therapeutically effective amount of an M1 receptor antagonist, a prolactin inhibitor, an agent acting on the ATP-dependent potassium channel of β-cells, metformin, a glucosidase inhibitor or a combination of any of them.

In certain embodiments, the invention relates to a method for inhibiting the proteolytic activity of a proteasome, DP8, DP9, or prostate specific antigen, comprising contacting a proteasome, DP8, DP9, or prostate specific antigen with any one of the aforementioned compounds.

In certain embodiments, the invention relates to a method for inhibiting the proteolytic activity of a proteasome, DP8, DP9, or prostate specific antigen in a patient, comprising administering to a patient in need thereof a therapeutically effective amount of any one of the aforementioned compounds.

In certain embodiments, the invention relates to any one of the aforementioned methods, wherein the compound is administered at a predetermined interval(s) during a 24-hour period, in an amount effective to improve one or more aberrant indices associated with glucose metabolism disorders (e.g., glucose intolerance, insulin resistance, hyperglycemia, hyperinsulinemia, and Type II diabetes). The effective amount of the compound may be about 0.01, 0.1, 1, 10, 30, 50, 70, 100, 150, 200, 500, or 1000 mg/kg of the subject.

In certain embodiments, the invention relates to a single administration any one of the aforementioned compounds. In certain embodiments, the invention relates to any one of the aforementioned single administrations, wherein the single administration is in the form of a bolus injection, oral dosage or inhaled dosage. In certain embodiments, the invention relates to any one of the aforementioned single administrations, wherein the single administration can produce a sustained in vivo effect.

EXEMPLIFICATION

The invention now being generally described, it will be more readily understood by reference to the following examples which are included merely for purposes of illustration of certain aspects and embodiments of the present invention, and are not intended to limit the invention.

Example 1

Synthesis of Glu-boroSar(thioxo amide)Hydrochloride

The synthetic scheme for the formation of compound 5 (Formula III) is shown in FIG. 1.

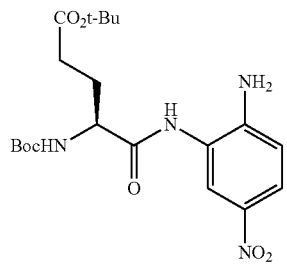

1

Compound 1. N-methylmorpholine (81.4 mL, 740 mmol) was added to a solution of N-Boc-L-Glu(O-t-Bu)-OH (112.5 g, 370 mmol) in THF (3000 mL) at −20° C., followed by dropwise addition of isobutyl chloroformate (48.1 mL, 370 mmol). The mixture was stirred for 20 min, then 4-nitro-1,2-phenylenediamine (56.6 g, 370 mmol) was added in portions, the resulting slurry was stirred at −15° C. for 2 h and then at r.t. overnight. The precipitate was filtered off, and the filtrate was evaporated to dryness. The residue was dissolved in EtOAc (2500 mL), washed successively with 1M $NaH_2PO_4$ (2×500 mL), brine (300 mL), 5% $NaHCO_3$ (2×500 mL) and brine (2×300 mL). The organic phase was dried with $Na_2SO_4$ and evaporated to dryness. Crystallization of the residue from EtOAc/hexane afforded compound 1 as a yellow powder (156 g, 96%).

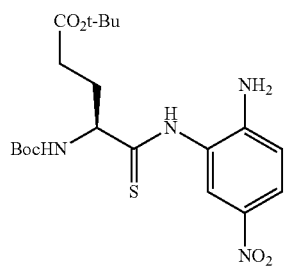

2

Compound 2. Under Argon, $P_4S_{10}$ (79.1 g, 178 mmol) was mixed with $Na_2CO_3$ (19 g, 178 mmol) in THF (3000 mL). The mixture was stirred for 1.5 h at 25° C. and then cooled to 0° C. To this clear solution anilide 1 (156 g, 356 mmol) in THF (500 mL) was added dropwise and the reaction was stirred at 0° C. for 30 min, then at r.t. for 3 h. The mixture was filtered through Celite, and filtrate was evaporated to dryness. The residue was dissolved in EtOAc/heptane (2/1, 2500 mL) and washed with 5% NaHCO$_3$ (3×500 mL), and the aqueous layers was back-extracted with EtOAc/heptane (2/1, 3×800 mL). The combined organic layers were washed with brine (2×300 mL), dried with Na$_2$SO$_4$, and evaporated to an oil. Crystallization of the residue from EtOAc/hexane afforded compound 2 as a yellow powder (143.2 g, 88.5%).

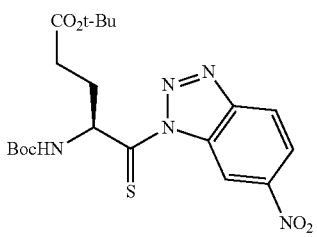

3

Compound 3. Thioanilide 2 (71 g, 156 mmol) was dissolved in 70% acetic acid (860 mL glacial acetic acid and 370 mL water) by gentle warming at 40° C. and then cooled to 3° C. by ice water. To this solution NaNO$_2$ (17 g, 246 mmol) was added in portions over 30 min with stirring. After reacted at the same temperature for another 1 h, iced water (4000 mL) was added portionwise, the resulting precipitated product was filtered and washed with cold water. The orange solid was redissolved in EtOAc (1500 mL), washed successively with 5% NaHCO$_3$ (2×300 mL), brine (2×300 mL). The organic phase was dried with Na$_2$SO$_4$ and evaporated under vacuum to afford compound 3 as a yellow powder (48.3 g, 66.5%).

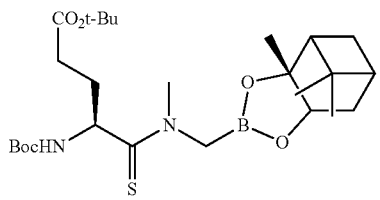

4

Compound 4. Et$_3$N (29 mL, 208 mmol) was added dropwise to a solution of compound 3 (48.3 g, 103.7 mmol) and boroSar-pn.HCl (29.6 g, 114 mmol) in THF (600 mL) under ice water bath. The reaction mixture was then allowed to be stirred at r.t. for 1 h. The precipitated salt was removed by filtration and the solvent was evaporated under vacuum. The residue was redissolved in EtOAc (1500 mL), washed successively with 0.1 N KHSO$_4$ (2×300 mL), sat. aq. NaHCO$_3$ (2×300 mL), brine (300 mL) and then dried with Na$_2$SO$_4$. Evaporation of the solvent and purification of the residue by silica gel chromatography column (hexane/EtOAc, 3:1) afforded the thiopeptide B (33.5 g, 61%).

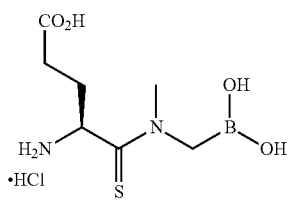

5

Glu-boroSar[thioxo amide]hydrochloride (5). To the ice water cooled solution of compound 4 (33.5 g, 63.8 mmol) in anhydrous dichloromethane (400 mL), HCl gas was bubbled for about 1 h or until saturated. The reaction mixture was allowed to be stirred at r.t. for 1.5 h and then was concentrated under reduced pressure to dryness to afford a white powder which was dissolved in pre-cooled 0.01 N HCl (200 mL). Then, tert-Butyl methyl ether (MTBE) (200 mL) and phenylboronic acid (7.1 g) were added. The mixture was stirred at room temperature for 1 h and the aqueous phase was separated. The MTBE layer was extracted with 0.05 N HCl (50 mL) and the combined aqueous phases were washed with ethyl ether (3×200 mL). Concentrated the aqueous phase on rotovap (<25° C.) and the crude product was purified by preparative HPLC eluted with 2% solvent B (solvent A, 1.8 mL HCl in 4 L water; solvent B, 1.2 mL HCl in 4 L acetonitrile). Collected the desired fractions and concentrated to approximately 60 mL and freeze dry. The resulted white powder was continued to be dried in a desiccator (NaOH & Drierite) under vacuum to give compound 5 (13.2 g, 76.5% over two steps). HPLC-TAN purity: 94.0% (linear form), 6.0% (cyclic form).

Figure 2:
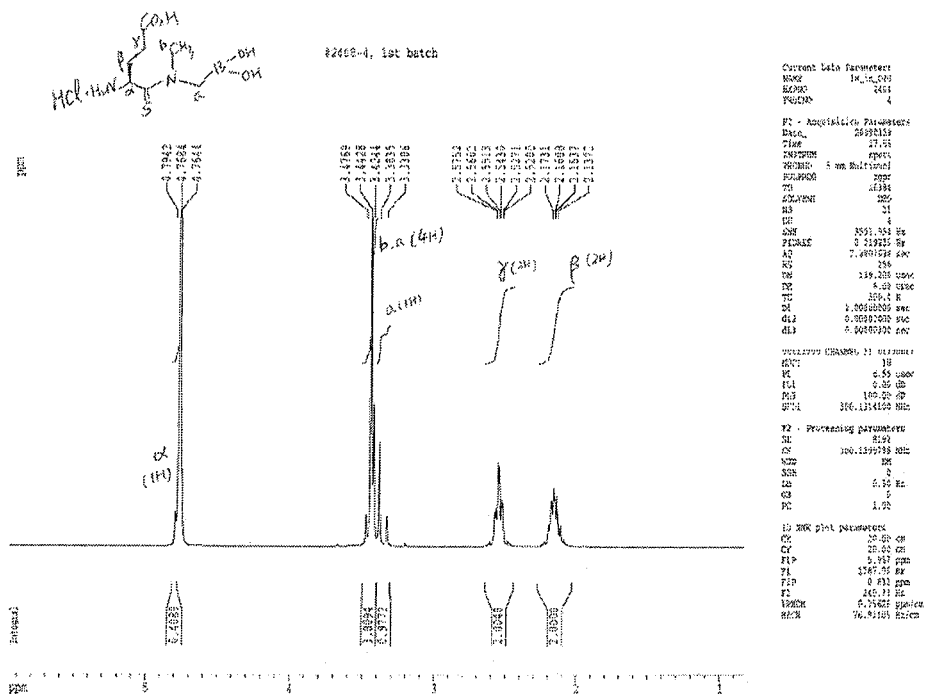
FIG. 2 depicts a $^1H$ NMR spectrum of compound 5 in $D_2O$.

The $^1$H NMR spectrum in D$_2$O of compound 5 is shown in FIG. 2.

Figure 3:
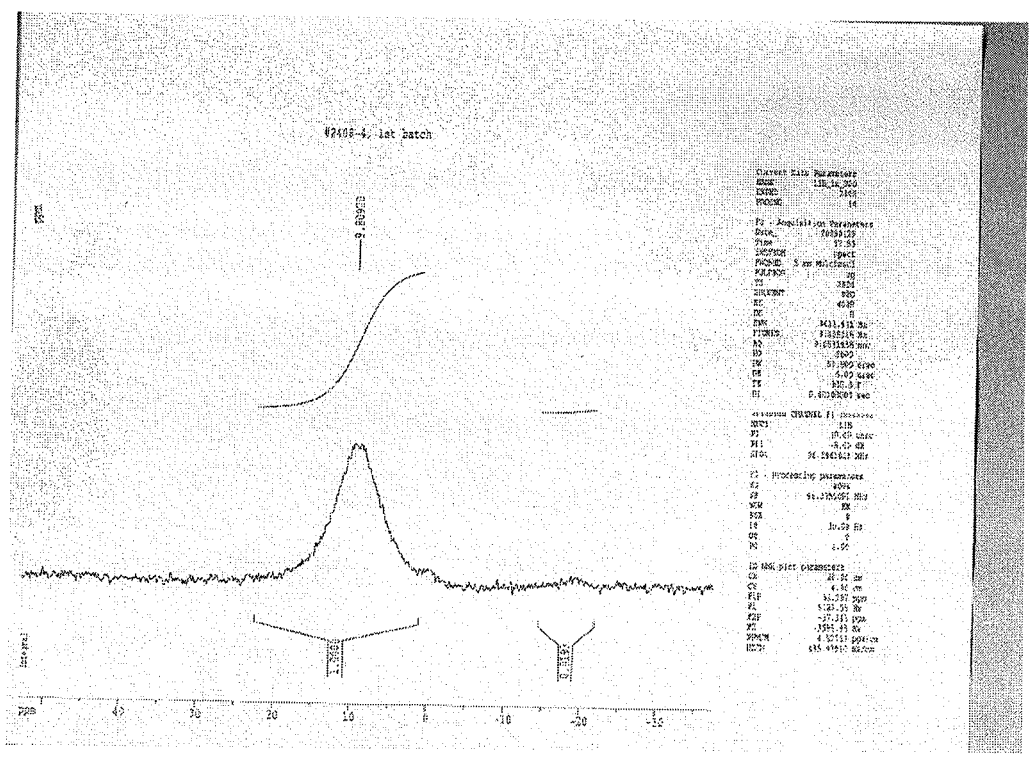
FIG. 3 depicts a $^{11}B$ NMR spectrum of compound 5 in $D_2O$.

The $^{11}$B NMR spectrum in D$_2$O of compound 5 is shown in FIG. 3.

Figure 4:
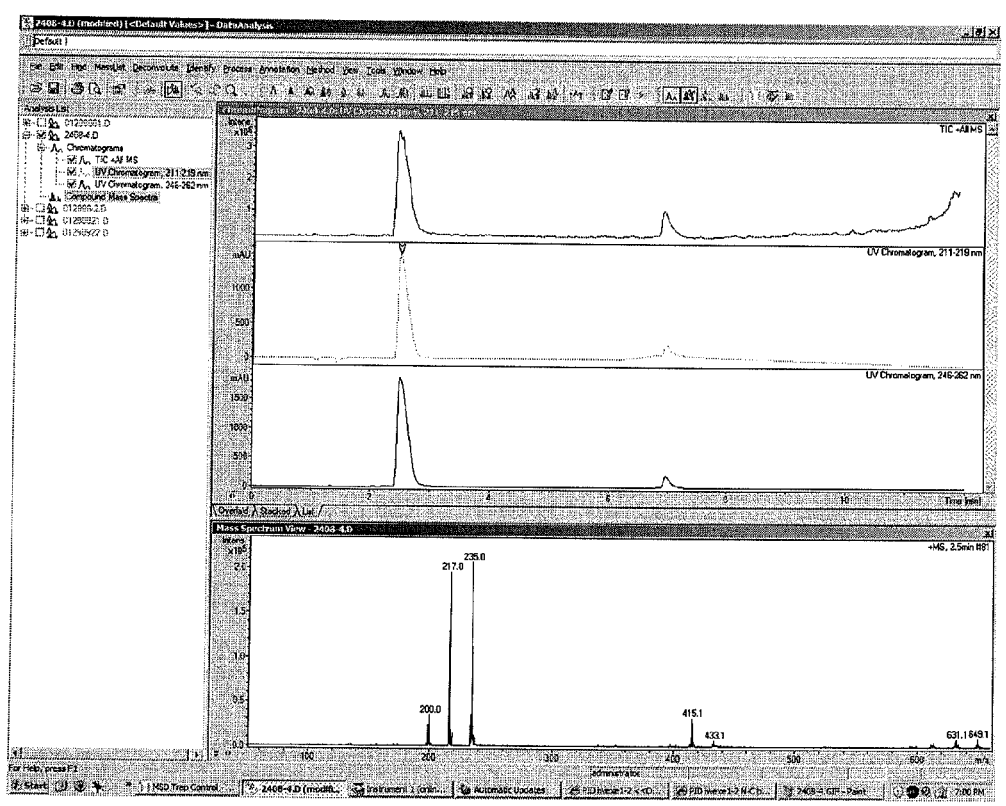
FIG. 4 depicts a LC-MS spectrum of compound 5.

The LC-MS spectrum of compound 5 is shown in FIG. 4.

Figure 5:
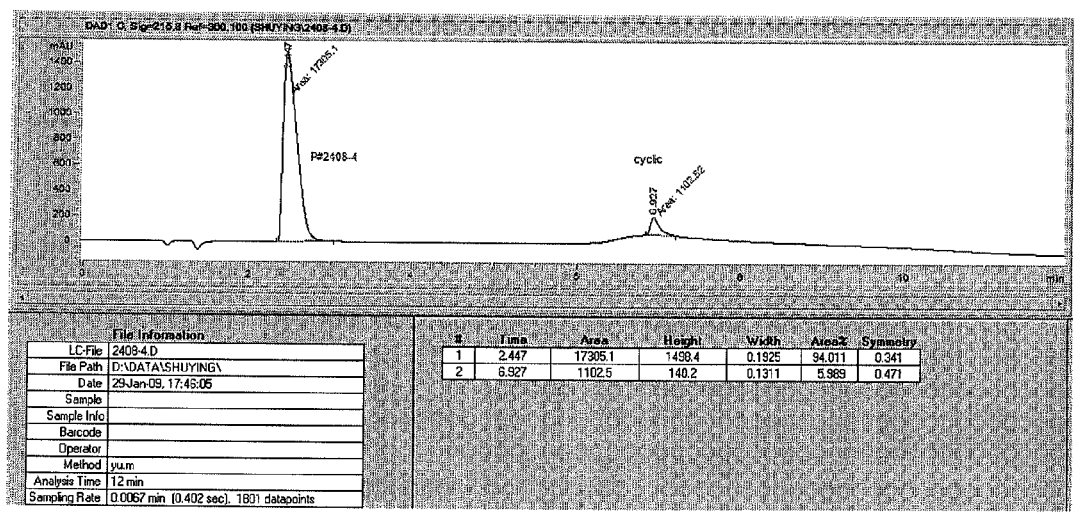
FIG. 5 depicts a HPLC chromatogram of compound 5.

The HPLC spectrum of compound 5 is shown in FIG. 5.

Example 2

In Vitro Assays

The methods of biological testing used are described in International Patent Application PCT/US06/047853, published as WO/2007/100374, which claims priority to U.S. Provisional Patent Application No. 60/752,017. These methods are herein incorporated in their entirety by reference.

FIGS. 6-9 depict the results from various biological assays. The CLogP values in these figures were calculated using ChemDraw Ultra version 11.0.

Specifically, attention is drawn to compound 5 (FIG. 7, first row) in comparison to its oxy-analog 11 (FIG. 6, bottom row). Compound 5 is a more potent inhibitor of DPP IV than compound 11, by about 66-fold.

Furthermore, compound 5 showed better selectivity for inhibiting DPP IV, than for either DPP8 or DPP9, making it much more selective for DPP IV than 11 (5 is 6,000× more potent for DPP IV than for DPP9, and 13,000× more potent for DPP IV than for DPP8; whereas 11 is only 430× and 2,000× more potent for DPP IV than for either DPP9 or DPP8, respectively).

Compound 5 also demonstrated good selectivity against FAP and PREP in vitro, a property that the boroPro compounds (6, 7, 8, 9, 10, 12, and 13) do not have.

Example 3

Toxicity

It has been hypothesized that the "Intracellular IC$_{50}$" parameter correlates with toxicity in vivo. Compound 5, therefore, exhibited essentially the most favorable intracellular IC$_{50}$ (IC-IC$_{50}$) value, in terms of toxicity, of the compounds listed in FIGS. 6-9. It is important to note that IC-IC$_{50}$ is not a measure of cell permeability. Like IC$_{50}$, it is a composite of factors, including cell permeability, potency against DPP9, rate and equilibrium of the intramolecular cyclization reaction, and inhibitor stability, both intrinsic and intracellular. Additionally, the IC-IC$_{50}$ values found in FIGS. 6-9 are from compounds preincubated at pH 2.0 for 4 h.

Figure 10:
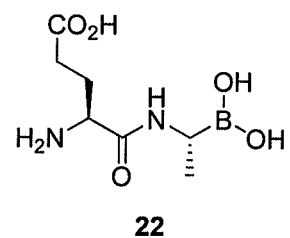
FIG. 10 depicts the structure of compound 22.
Figure 11:
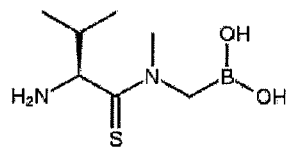
FIG. 11A-C depicts the structure of compound 23, Val-boroSar (thioxo amide) (A), synthetic route to 23 (B), and DPPIV assay results at pH=2 and 8 (C).
Figure 11:
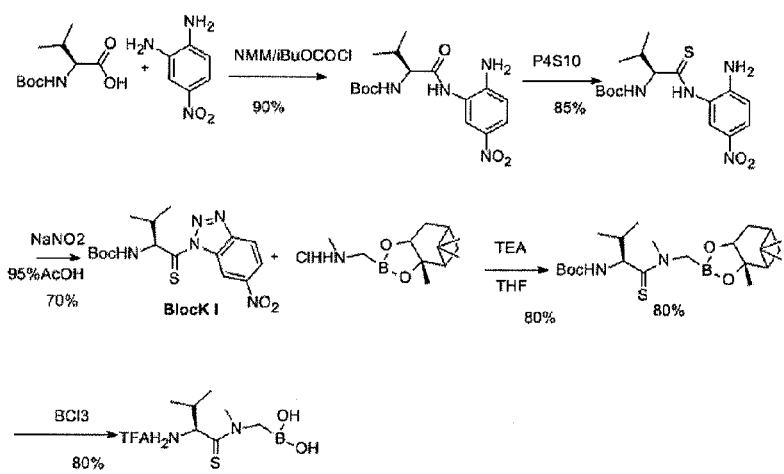
Figure 11:
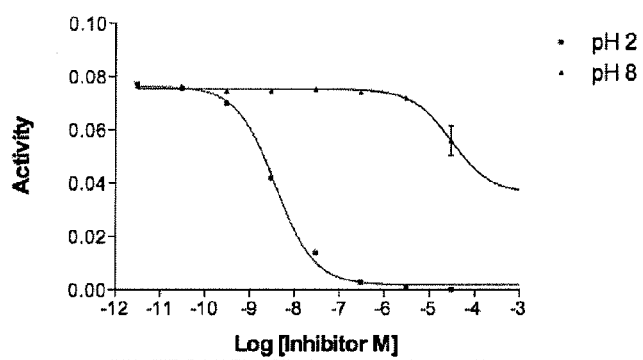
Figure 12:
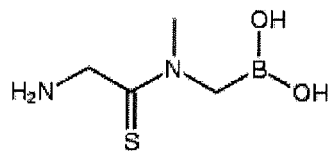
FIG. 12 A-C depicts the structure of compound 24, Gly-boroSar (thioxo amide) (A), synthetic route to 24 (B), and DPPIV assay results at pH=2 (C).
Figure 12:
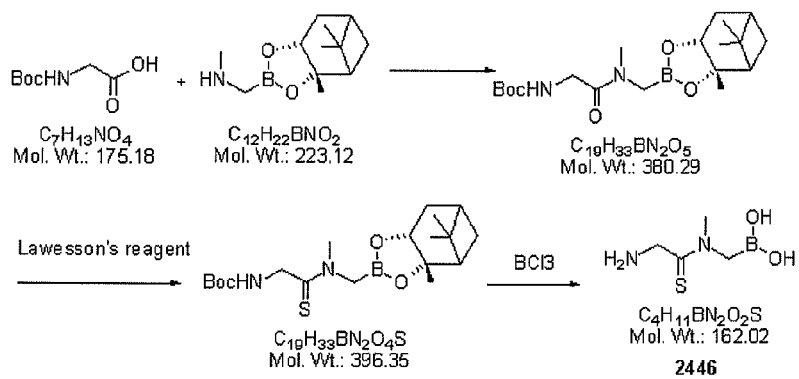
Figure 12:
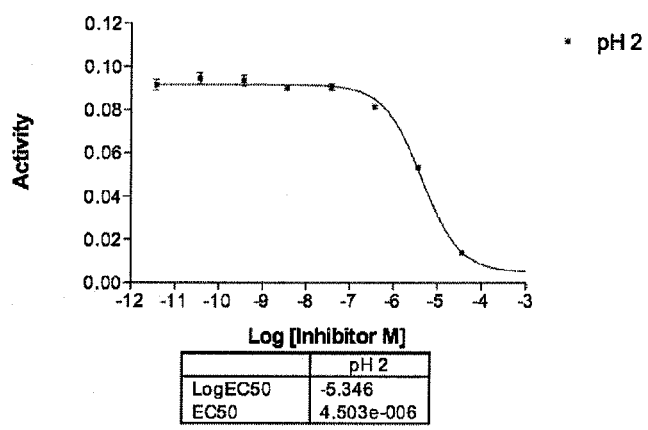
Figure 13:
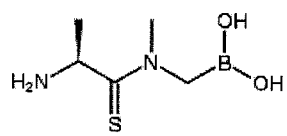
FIG. 13 A-C depicts the structure of compound 25, Ala-boroSar (thioxo amide) (A), synthetic route to 25 (B), and DPPIV assay results at pH=2 and 8 (C).
Figure 13:
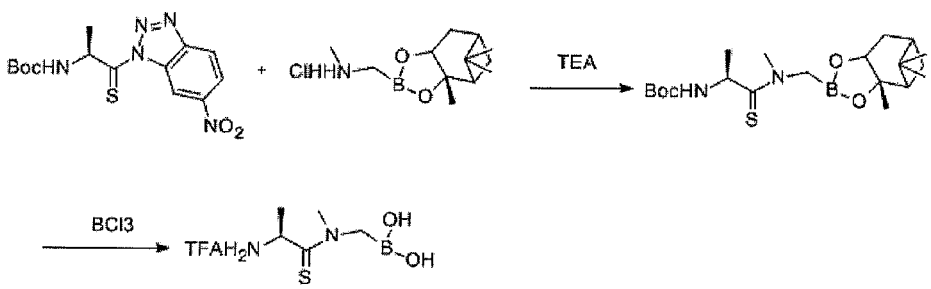
Figure 13:
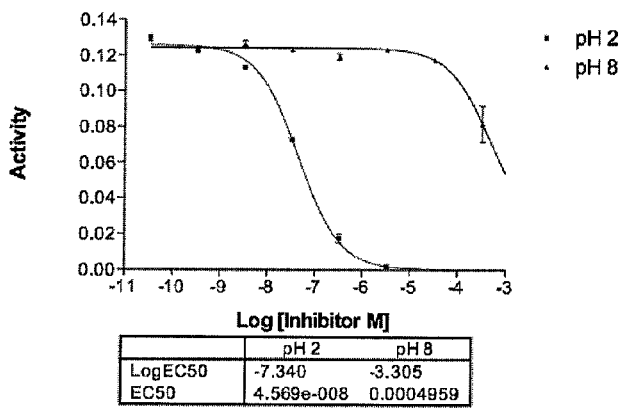
Figure 14:
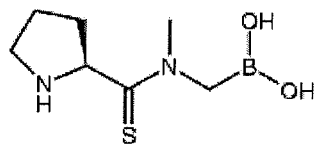
FIG. 14 A-C depicts the structure of compound 26, Pro-boroSar (thioxo amide) (A), synthetic route to 26 (B), and DPPIV assay results at pH=2 and 8 (C).
Figure 14:
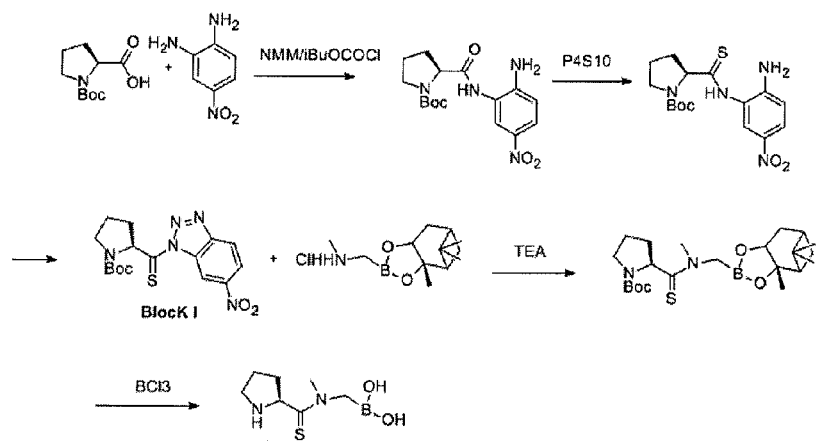
Figure 14:
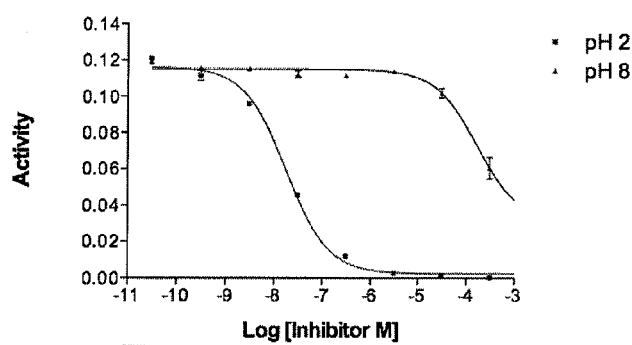
Figure 15:
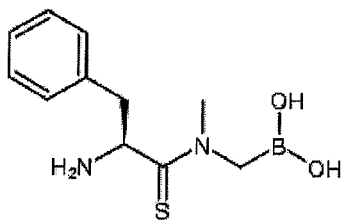
FIG. 15 A-B depicts the structure of compound 27, Phe-boroSar (thioxo amide) (A), and DPPIV assay results at pH=2 and 8 (B).
Figure 15:
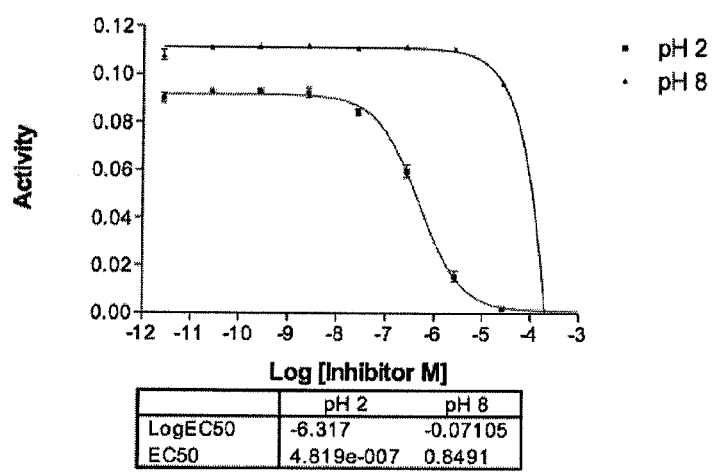
Figure 16:
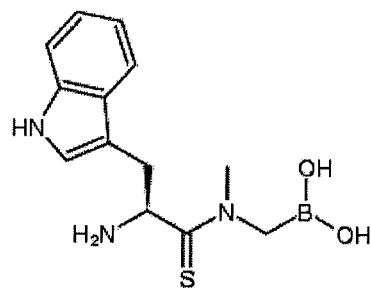
FIG. 16 A-B depicts the structure of compound 28, Trp-boroSar (thioxo amide) (A), and synthetic route to 28 (B).
Figure 16:
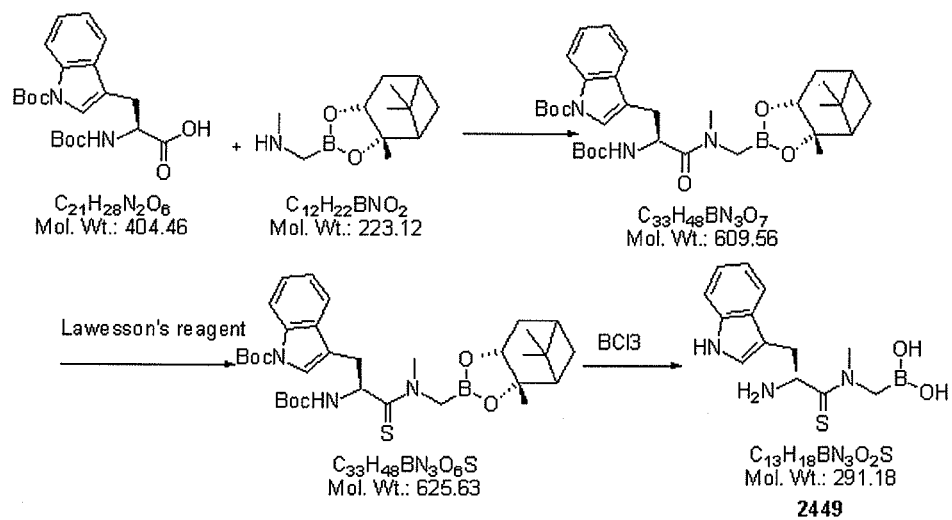
Figure 17:
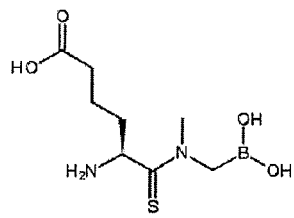
FIG. 17 A-C depicts the structure of compound 29, 2-aminoadipic-boroSar (thioxo amide) or 2-Aad-boroSar (thioxo amide) (A), synthetic route to 29 (B), and IC50 values for DPP 4/8/9 assay results (C).
Figure 17:
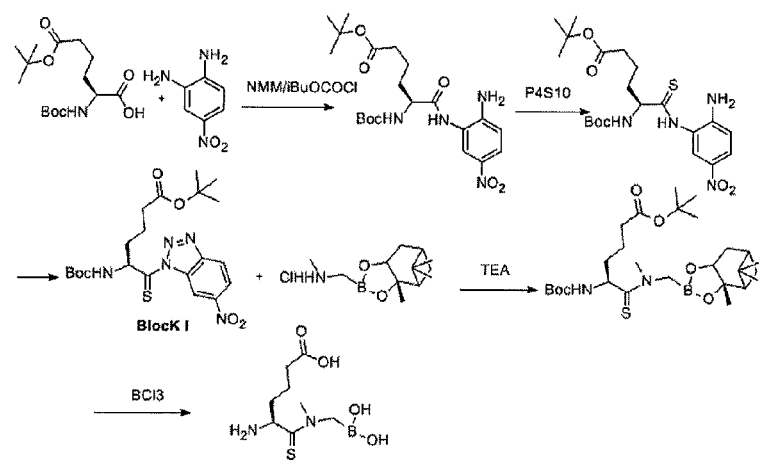
Figure 17:
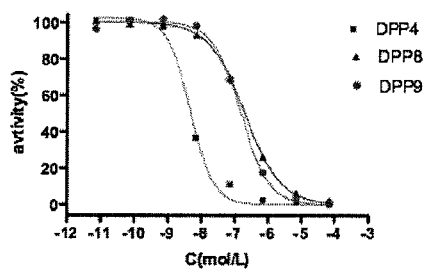
Figure 18:
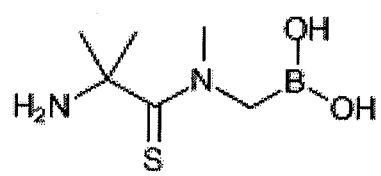
FIG. 18 depicts the structure of compound 30, Aib-boroSar (thioxo amide)

As a measure of toxicity, the maximum tolerated doses (MTD) of compounds 6, 7, and 22 (compound 22 is depicted in FIG. 10) were determined in escalating single-dose studies, using Sprague-Dawley (SD) rats. Compound 6 was tolerated least well, with a MTD of 0.025 mg/kg. The initial signs of toxicity were observed 3-4 h postdose, and consisted mainly of severely decreased activity. Necroscopy performed on lethargic animals showed vasocongestion of all abdominal and thoracic organs, and presence of clear fluid in stomach and small intestines, indicative of gastrointestinal (GI) toxicity. Compound 7 exhibited a MTD of $\geq$5 mg/kg—at least 200-fold greater than that of 6. Several rats that received more than 5 mg/kg exhibited lethargy and were sacrificed and necroscopied. Fluid and gas were found in the intestine and cecum, again indicative of GI toxicity. Rats receiving compound 22 exhibited no adverse effects until doses exceeded 500 mg/kg, yielding a MTD >$2.0\times10^4$-fold that of 6 and between 13- to 100-fold greater than that of 7. At 900 mg/kg of 22, three of six animals died. There were no obvious signs of premortem suffering or other adverse side effects. Necroscopies revealed that the deceased rats had fluid-filled stomachs and small intestines, indicative of gastrointestinal toxicity. All other organs appeared normal.

Compound 6 exhibited the most effective IC-IC$_{50}$ of the compounds tested, 80 nM. As described above, compound 6 is also the most toxic. Compound 7 exhibited an IC-IC$_{50}$ of 10.3 μM. The estimated IC-IC$_{50}$ of compound 22 is >7000 μM. A correlation exists between the IC-IC$_{50}$ and MTD values. Intracellular potency against DPP9, as measured by the IC-IC$_{50}$ values, decreases in the order 6>7>22, the same as for the MTDs, showing that intracellular potency of these inhibitors tracks their toxicites qualitatively.

A discussion of the IC-IC$_{50}$ measurements and the correlation between the demonstrated IC-IC$_{50}$ values and the MTDs can be found in *J. Med. Chem.* 2008, 51(19), 6005, which is hereby incorporated in its entirety by reference.

Furthermore, compound 8, with an IC-IC$_{50}$ of 199 nM is also very effective. Studies in monkeys have shown that compound 8 is also very toxic.

The IC-IC$_{50}$ of compound 5, however, is 828 μM, indicating that compound 5 is not very effective at inhibiting DPP9 intracellularly. Indeed, compound 14 is a known antidiabetic drug, sitagliptin (DPP IV inhibitor). Its IC-IC$_{50}$ was measured to be 213 μM. Based on this measurement, compound 5 should be less effective than compound 14.

The IC-IC$_{50}$ demonstrated by compound 5, however, indicates that compound 5 should exhibit minimal toxicity, as determined by the measured MTD. Preliminary results indicate that this is the case. In an experiment, 13 male SD rats were given 300 mg/kg of compound 5. After 24 h, all animals were behaving normally with no sign of toxicity. As a comparison, compound 6 kills rats at a single dose of 0.05 mg/kg.

Incorporation by Reference

All of the U.S. patents and U.S. patent application publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:
1. A compound represented by Formula II:

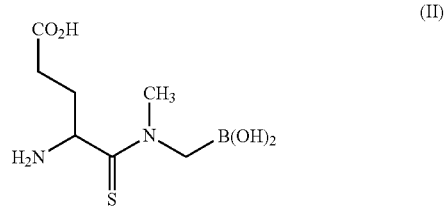

or a pharmaceutically acceptable salt thereof.
2. The compound of claim 1, wherein the compound is represented by Formula III:

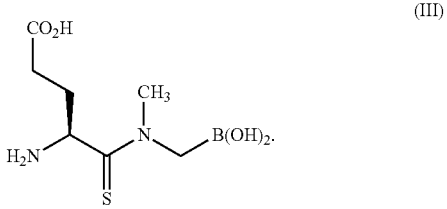

* * * * *